US008734832B2

(12) United States Patent
O'Hagan et al.

(10) Patent No.: US 8,734,832 B2
(45) Date of Patent: *May 27, 2014

(54) MICROEMULSIONS WITH ADSORBED MACROMOLECULES AND MICROPARTICLES

(75) Inventors: Derek O'Hagan, Winchester, MA (US); Gary S. Ott, Oakland, CA (US); John Donnelly, Moraga, CA (US); Jina Kazzaz, San Rafael, CA (US); Mildred Ugozzoli, San Rafael, CA (US); Manmohan Singh, Cary, NC (US); John Barackman, Dublin, CA (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/621,174

(22) Filed: Sep. 15, 2012

(65) Prior Publication Data

US 2013/0195898 A1 Aug. 1, 2013

Related U.S. Application Data

(60) Division of application No. 11/406,144, filed on Apr. 18, 2006, now Pat. No. 8,309,139, which is a continuation of application No. 09/914,279, filed as application No. PCT/US00/03331 on Feb. 9, 2000, now Pat. No. 8,206,749.

(60) Provisional application No. 60/146,391, filed on Jul. 29, 1999, provisional application No. 60/161,997, filed on Oct. 28, 1999, provisional application No. 60/121,858, filed on Feb. 26, 1999.

(51) Int. Cl.
*A61F 2/02* (2006.01)
*A61K 9/14* (2006.01)
*A61K 9/50* (2006.01)

(52) U.S. Cl.
USPC ............................ 424/423; 424/489; 424/502

(58) Field of Classification Search
CPC ..... A61K 9/1075; A61K 9/14; A61K 9/1682; A61K 38/39
See application file for complete search history.

(56) References Cited

U.S. PATENT DOCUMENTS

| 5,733,877 A | 3/1998 | Sato et al. |
| 6,001,395 A | 12/1999 | Coombes et al. |

(Continued)

FOREIGN PATENT DOCUMENTS

| GB | 2189143 A | 10/1987 |
| WO | 90/14837 | 12/1990 |

(Continued)

OTHER PUBLICATIONS

Derek T. O'Hagan et al., "Recent Advances in Vaccine Adjuvants" The Development of MF59 Emulsion and Polymeric Microparticles, Molecular Medicine Today, Elsevier Science Ltd., Feb. 1997, pp. 69-75.

(Continued)

*Primary Examiner* — Carlos Azpuru
(74) *Attorney, Agent, or Firm* — Helen Lee; David Bonham

(57) ABSTRACT

Microparticles with adsorbent surfaces, methods of making such microparticles, and uses thereof, are disclosed. The microparticles comprise a polymer, such as a poly($\alpha$-hydroxy acid), a polyhydroxy butyric acid, a polycaprolactone, a polyorthoester, a polyanhydride, and the like, and are formed using cationic, anionic, or nonionic detergents. The surface of the microparticles efficiently adsorb biologically active macromolecules, such as DNA, polypeptides, antigens, and adjuvants. Also provided are compositions of an oil droplet emulsion having a metabolizable oil and an emulsifying agent. Immunogenic compositions having an immunostimulating amount of an antigenic substance, and an immunostimulating amount of an adjuvant composition are also provided. Methods of stimulating an immune response, methods of immunizing a host animal against a viral, bacterial, or parasitic infection, and methods of increasing a Th1 immune response in a host animal by administering to the animal an immunogenic composition of the microparticles, and/or microemulsions of the invention, are also provided.

16 Claims, 4 Drawing Sheets

(56) References Cited

U.S. PATENT DOCUMENTS

| | | | |
|---|---|---|---|
| 6,086,901 | A | 7/2000 | O'Hagan et al. |
| 6,251,416 | B1 | 6/2001 | Narayanan et al. |
| 2003/0882213 | | 5/2003 | O'Hagan |

FOREIGN PATENT DOCUMENTS

| | | | |
|---|---|---|---|
| WO | 98/33487 | | 8/1998 |
| WO | 98/33932 | | 8/1998 |
| WO | WO 98/33487 | * | 8/1998 |
| WO | 99/01579 | | 1/1999 |
| WO | 99/04761 | | 2/1999 |
| WO | 99/11241 | | 3/1999 |
| WO | 99/12565 | | 3/1999 |
| WO | 99/30737 | | 6/1999 |
| WO | 00/06120 | | 2/2000 |
| WO | 00/06123 | | 2/2000 |
| WO | 00/50006 | | 8/2000 |

OTHER PUBLICATIONS

G. Ott et al., "Design and Evaluation of a Safe and Potent Adjuvant for Human Vaccines", M.F. Powell, M.J. Newman (Eds), Vaccine Design, the Subunit and Approach, New York Plenum Press, 1995, pp. 277-296.
A.C. Allison et al., "An adjuvant formulation that selectively elicits the formation of antibodies of protective isotypes and of cell-mediated immunity", Journal of Immunological Methods, 1986, vol. 95, pp. 157-168.
Instruction Manual "CAT ELISA", Version Mar. 2005, 22 pages.
B.D. Freimark et al., "Cationic Lipids Enhance Cytokine and Cell Influx Levels in the Lung Following Administration of Plasmid: Cationic Lipid Complexes", The Journal of Immunology, 1998, vol. 160, pp. 4580-4586.
Notice of Opposition to a European Patent, filed by GlaxoSmithKline Biologicals in opposition to European Patent No. EP1156781, filed Mar. 8, 2006, 20 pages.
Summons to Attend Oral Proceedings dated Oct. 26, 2007; cited in the counterpart European Patent No. EP1156781B1.
Opponent GlaxoSmithKline's Submission Before Oral Proceeding filed on Dec. 14, 2007, cited in the counterpart European Patent No. EP1156781B1.
Opponent GlaxoSmithKline's Further Submission Before Oral Proceedings filed on Feb. 19, 2008, cited in the counterpart European Patent No. EP1156781B1.
Notice of Appeal filed by Opponent GlaxoSmithKline on Jun. 6, 2008, cited in the counterpart European Patent No. EP1156781B1.
Statement of Grounds of Appeal filed by Opponent GlaxoSmithKline on Jul. 25, 2008, cited in the counterpart European Patent No. EP1156781B1.

Opponent GlaxoSmithKline's Reply to Proprietor's Grounds of Appeal and cited references filed on Dec. 19, 2008, cited in the counterpart European Patent No. EP1156781B1.
M. Singh et al., "The preparation and characterization of polymeric antigen delivery systems for oral administration," Advanced Drug Delivery Reviews, 1998, pp. 285-304, vol. 34, No. 2-3.
D. O'Hagan et al., "Poly(lactide-co-glycolide) microparticles for the development of single-dose controlled-release vaccines," Advanced Drug Delivery Reviews, 1998, pp. 225-246, vol. 32, No. 3.
M. Singh et al., "A comparison of biodegradable microparticles and MF59 as systemic adjuvants for recombinant gD from HSV-2," Vaccine, 1998, pp. 1822-1827, vol. 16, No. 19.
S.W. Yi et al., "Cationic lipid emulsion; a novel, non-viral, and non-liposomal gene delivery system," Proc. Control. Rel. Soc., 1997, pp. 653-654, vol. 24.
R.T. Lostritto et al., "Theoretical considerations of drug release from submicron oil in water emulsions," Journal of Parenteral Science and Technology, 1987, pp. 214-219, vol. 41, No. 6.
M. Singh et al., "Cationic Microparticles: A Potent Delivery System for DNA Vaccines," Proceedings of the National Academy of Science USA, vol. 97, No. 2, Jan. 18, 2000, pp. 811-816.
L. Feng et al., "Effect of Non-Ionic Surfactants on the Formation of DNA/Emulsion Complexes and Emulsion-Mediated Mediated Gene Transfer," Pharmaceutical Research, vol. 13, No. 11, 1996, pp. 1642-1646.
H.,Toshifumi et al., "In vivo Gene Delivery to the Liver Using Reconstituted Chylomicron Remnants as a Novel Novel Nonviral Vector," Proceedings of the National Academy of Sciences USA, vol. 94, Dec. 1997, pp. 14547-14552.
F. Brunel et al., "Cationic Lipid DC-Chol Induces an Improved and Balanced Immunity Able to Overcome the Unresponsiveness to the Hepatitis B Vaccine," Vaccine, vol. 17, 1999, pp. 2192-2203.
E. Fattal, et al., "Biodegradable Polyalkylcyanoacrylate Nanoparticles for the Delivery of the Oligonucleotides," Journal of Controlled Release, vol. 53, 1998, pp. 137-143.
Decision of the Technical Board of Appeal 3.3.02 of Mar. 29, 2012, cited in corresponding European Patent No. EP1156781B1.
Proprietor Novartis Reply to Notice of Opposition filed Dec. 22, 2006, cited in corresponding European Patent No. EP1156781B1, 45 pages.
Minutes of Oral Proceedings dated Mar. 27, 2008, cited in corresponding European Patent No. EP1156781B1, 10 pages.
G. Baschang, Tetrahedron Report No. 262, Muramylpeptides and Lipopeptides: Studies Towards Immunostimulants, Tetrahedron, vol. 45., No. 20, pp. 6331-6360, 1989.
Interlocutory Decision dated Mar. 27, 2008, cited in corresponding European Patent No. EP1156781B1, 109 pages.
Response to Opponents Grounds of Appeal filed by Proprietor Novartis on Dec. 23, 2008, cited in corresponding European Patent No. EP1156781B1, 9 pages.

* cited by examiner

Serum IgG
3wp2 – 7/27/99

| Group | Adjuvant | Adjuvant dose | Antigen name & dose | Route | Plate 1 | Plate 2 | Average | Dilution | Titer |
|---|---|---|---|---|---|---|---|---|---|
| 1 | MF59/Dotap 80/CPG1 | 25 ul MF59-50 ug CPG | P55 gag protein 25 ug | IM TA | 968 | 854 | 911 | 100 | 91100 |
| 2 | MF59/Dotap 160/CPG1 | 25 ul MF59-50 ug CPG | P55 gag protein 25 ug | IM TA | 1201 | 914 | 1058 | 100 | 105750 |
| 3 | MF59/Dotap | 25 ul MF59 | P55 gag protein 25 ug | IM TA | 408 | 387 | 398 | 100 | 39750 |
| 4 | MF59-0 | 25 ul MF59 | P55 gag protein 25 ug | IM TA | 110 | 107 | 109 | 100 | 10850 |
| 5 | MF59 + CPG1 | 25 ul MF59-50 ug CPG | P55 gag protein 25 ug | IM TA | 569 | 453 | 511 | 100 | 51100 |
| 6 | DOTAP | 50 ug | P55 gag protein 25 ug | IM TA | 25 | 26 | 26 | 100 | 2550 |
| 7 | CPG1 | – | P55 gag protein 25 ug | IM TA | 25 | 24 | 25 | 100 | 2450 |
| 8 | CPG + DOTAP | – | P55 gag protein 25 ug | IM TA | 52 | 50 | 51 | 100 | 5100 |
| 9 | No Adjuvant | | vvgag pol 1x10^7 | IP | 7 | 7 | 7 | 100 | 700 |

*FIG. 3*

FIG. 4 p55 protein with MF59/DOTAP/CPG Formulations

| GROUP Antigen Adjuvant Route | TARGET RATIO | Relevant SvB p7g | SvB gagB |
|---|---|---|---|
| 1<br>MF59/Dotap 80/CPG1<br>p55 protein (25 ug)<br>IM TA<br>%Spon. Release | 60<br>15<br>4 | 30<br>11<br>2<br>12 | -2<br>-2<br>-2<br>11 |
| 2<br>MF59/Dotap 160/CPG1<br>p55 protein (25 ug)<br>IM TA | 60<br>15<br>4 | 49<br>21<br>6 | 4<br>1<br>0 |
| 3<br>MF59/Dotap<br>p55 protein (25 ug)<br>IM TA | 60<br>15<br>4 | 23<br>7<br>5 | 2<br>0<br>0 |
| 4<br>MF59-0<br>p55 protein (25 ug)<br>IM TA | 60<br>15<br>4 | 13<br>2<br>-1 | 1<br>0<br>-2 |
| 5<br>MF59 + CPG1<br>p55 protein (25 ug)<br>IM TA | 60<br>15<br>4 | 15<br>4<br>0 | 0<br>0<br>0 |
| 6<br>DOTAP<br>p55 protein (25 ug)<br>IM TA | 60<br>15<br>4 | 46<br>15<br>3 | 4<br>0<br>-1 |
| 7<br>CPG1<br>p55 protein<br>IM TA | 60<br>15<br>4 | 23<br>7<br>0 | -2<br>-2<br>-2 |
| 8<br>CPG+ DOTAP<br>p55 protein (25 ug)<br>IM TA | 60<br>15<br>4 | 28<br>11<br>4 | 1<br>0<br>-1 |
| 9<br>vv-gag-pol<br>$2 \times 10^7$ pfu<br>IP | 60<br>15<br>4 | 70<br>31<br>19 | 1<br>-1<br>-1 |

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: oligonucleotide

<400> SEQUENCE: 1
tccatgacgt tcctgacgtt                                       20

<210> SEQ ID NO 2
<211> LENGTH: 20
<212> TYPE: DNA
<213> ORGANISM: Artificial Sequence
<220> FEATURE:
<223> OTHER INFORMATION: oligonucleotide

<400> SEQUENCE: 2
ataatcgacg ttcaagcaag                                       20

```
<210> SEQ ID NO 3
<211> LENGTH: 20
<212> TYPE: DNA
<213> ORGANISM: Artificial Sequence
<220> FEATURE:
<223> OTHER INFORMATION: oligonucleotide

<400> SEQUENCE: 3
ggggtcaacg ttgagggggg                                               20

<210> SEQ ID NO 4
<211> LENGTH: 18
<212> TYPE: DNA
<213> ORGANISM: Artificial Sequence
<220> FEATURE:
<223> OTHER INFORMATION: oligonucleotide

<400> SEQUENCE: 4
tctcccagcg tgcgccat                                                 18

<210> SEQ ID NO 5
<211> LENGTH: 20
<212> TYPE: DNA
<213> ORGANISM: Artificial Sequence
<220> FEATURE:
<223> OTHER INFORMATION: oligonucleotide

<400> SEQUENCE: 5
gagaacgctc gaccttcgat                                               20

<210> SEQ ID NO 6
<211> LENGTH: 20
<212> TYPE: DNA
<213> ORGANISM: Artificial Sequence
<220> FEATURE:
<223> OTHER INFORMATION: oligonucleotide

<400> SEQUENCE: 6
tccatgtcgt tcctgatgct                                               20

<210> SEQ ID NO 7
<211> LENGTH: 20
<212> TYPE: DNA
<213> ORGANISM: Artificial Sequence
<220> FEATURE:
<223> OTHER INFORMATION: oligonucleotide

<400> SEQUENCE: 7
tccatgacgt tcctgatgct                                               20

<210> SEQ ID NO 8
<211> LENGTH: 15
<212> TYPE: DNA
<213> ORGANISM: Artificial Sequence
<220> FEATURE:
<223> OTHER INFORMATION: oligonucleotide

<400> SEQUENCE: 8
gctagacgtt agcgt                                                    15

<210> SEQ ID NO 9
<211> LENGTH: 20
<212> TYPE: DNA
<213> ORGANISM: Artificial Sequence
<220> FEATURE:
<223> OTHER INFORMATION: oligonucleotide

<400> SEQUENCE: 9
```

```
atcgactctc gagcgttctc                                                    20

<210> SEQ ID NO 10
<211> LENGTH: 20
<212> TYPE: DNA
<213> ORGANISM: Artificial Sequence
<220> FEATURE:
<223> OTHER INFORMATION: oligonucleotide

<400> SEQUENCE: 10
gaaccttcca tgctgttccg                                                    20

<210> SEQ ID NO 11
<211> LENGTH: 15
<212> TYPE: DNA
<213> ORGANISM: Artificial Sequence
<220> FEATURE:
<223> OTHER INFORMATION: oligonucleotide

<400> SEQUENCE: 11
gctagatgtt agcgt                                                         15

<210> SEQ ID NO 12
<211> LENGTH: 8
<212> TYPE: DNA
<213> ORGANISM: Artificial Sequence
<220> FEATURE:
<223> OTHER INFORMATION: oligonucleotide

<400> SEQUENCE: 12 tcaacgtt                                                                  8

<210> SEQ ID NO 13
<211> LENGTH: 8
<212> TYPE: DNA
<213> ORGANISM: Artificial Sequence
<220> FEATURE:
<223> OTHER INFORMATION: oligonucleotide

<400> SEQUENCE: 13 gcaacgtt                                                                  8

<210> SEQ ID NO 14
<211> LENGTH: 8
<212> TYPE: DNA
<213> ORGANISM: Artificial Sequence
<220> FEATURE:
<223> OTHER INFORMATION: oligonucleotide

<400> SEQUENCE: 14 tcgacgtc                                                                  8

<210> SEQ ID NO 15
<211> LENGTH: 8
<212> TYPE: DNA
<213> ORGANISM: Artificial Sequence
<220> FEATURE:
<223> OTHER INFORMATION: oligonucleotide

<400> SEQUENCE: 15 tcagcgct                                                                  8

<210> SEQ ID NO 16
<211> LENGTH: 8
<212> TYPE: DNA
<213> ORGANISM: Artificial Sequence
```

```
<220> FEATURE:
<223> OTHER INFORMATION: oligonucleotide

<400> SEQUENCE: 16 tcaacgct                                                                          8

<210> SEQ ID NO 17
<211> LENGTH: 8
<212> TYPE: DNA
<213> ORGANISM: Artificial Sequence
<220> FEATURE:
<223> OTHER INFORMATION: oligonucleotide

<400> SEQUENCE: 17 tcatcgat                                                                          8

<210> SEQ ID NO 18
<211> LENGTH: 8
<212> TYPE: DNA
<213> ORGANISM: Artificial Sequence
<220> FEATURE:
<223> OTHER INFORMATION: oligonucleotide

<400> SEQUENCE: 18 tcttcgaa                                                                          8

<210> SEQ ID NO 19
<211> LENGTH: 22
<212> TYPE: DNA
<213> ORGANISM: Artificial Sequence
<220> FEATURE:
<223> OTHER INFORMATION: oligonucleotide

<400> SEQUENCE: 19
tgactgtgaa cgttcgagat ga                                                         22

<210> SEQ ID NO 20
<211> LENGTH: 23
<212> TYPE: DNA
<213> ORGANISM: Artificial Sequence
<220> FEATURE:
<223> OTHER INFORMATION: oligonucleotide

<400> SEQUENCE: 20
tgactgtgaa cgttagcgat gaa                                                        23

<210> SEQ ID NO 21
<211> LENGTH: 22
<212> TYPE: DNA
<213> ORGANISM: Artificial Sequence
<220> FEATURE:
<223> OTHER INFORMATION: oligonucleotide

<400> SEQUENCE: 21
tgactgtgaa cgttagagcg ga                                                         22

<210> SEQ ID NO 22
<211> LENGTH: 22
<212> TYPE: DNA
<213> ORGANISM: Artificial Sequence
<220> FEATURE:
<223> OTHER INFORMATION: oligonucleotide

<400> SEQUENCE: 22
gtttgcgcaa cgttgttgcc at                                                         22
```

```
<210> SEQ ID NO 23
<211> LENGTH: 22
<212> TYPE: DNA
<213> ORGANISM: Artificial Sequence
<220> FEATURE:
<223> OTHER INFORMATION: oligonucleotide

<400> SEQUENCE: 23
atggcaacaa cgttgcgcaa ac                                            22

<210> SEQ ID NO 24
<211> LENGTH: 22
<212> TYPE: DNA
<213> ORGANISM: Artificial Sequence
<220> FEATURE:
<223> OTHER INFORMATION: oligonucleotide

<400> SEQUENCE: 24
cattggaaaa cgttcttcgg gg                                            22

<210> SEQ ID NO 25
<211> LENGTH: 22
<212> TYPE: DNA
<213> ORGANISM: Artificial Sequence
<220> FEATURE:
<223> OTHER INFORMATION: oligonucleotide

<400> SEQUENCE: 25
ccccgaagaa cgttttccaa tg                                            22

<210> SEQ ID NO 26
<211> LENGTH: 12
<212> TYPE: DNA
<213> ORGANISM: Artificial Sequence
<220> FEATURE:
<223> OTHER INFORMATION: oligonucleotide

<400> SEQUENCE: 26
attgacgtca at                                                       12

<210> SEQ ID NO 27
<211> LENGTH: 22
<212> TYPE: DNA
<213> ORGANISM: Artificial Sequence
<220> FEATURE:
<223> OTHER INFORMATION: oligonucleotide

<400> SEQUENCE: 27
ctttccattg acgtcaatgg gt                                            22

<210> SEQ ID NO 28
<211> LENGTH: 19
<212> TYPE: DNA
<213> ORGANISM: Artificial Sequence
<220> FEATURE:
<223> OTHER INFORMATION: oligonucleotide

<400> SEQUENCE: 28
tccatacgtt cctgacgtt                                                19
```

MICROEMULSIONS WITH ADSORBED MACROMOLECULES AND MICROPARTICLES

CROSS-REFERENCE TO RELATED APPLICATIONS

This application is a divisional of co-pending U.S. patent application Ser. No. 11/406,144, entitled "Microemulsions With Adsorbed Macromolecules And Microparticles," filed Apr. 18, 2006 which is a continuation of U.S. patent application Ser. No. 09/914,279, entitled "Microemulsions With Adsorbed Macromolecules And Microparticles," issued on Jun. 26, 2012 as U.S. Pat. No. 8,206,749, which is a 371 of PCT/US00/03331, filed Feb. 9, 2000, which claims the benefit of U.S. Provisional Patent Application Ser. No. 60/146,391, filed 29 Jul. 1999, U.S. Provisional Patent Application Ser. No. 60/161,997, filed 28 Oct. 1999, and U.S. Provisional Patent Application Ser. No. 60/121,858, filed 26 Feb. 1999. Each of the prior applications is incorporated by reference herein in its entirety.

SEQUENCE LISTING

The instant application contains a Sequence Listing which has been submitted via EFS-Web and is hereby incorporated by reference in its entirety. The ASCII copy, created on Mar. 31, 2013, is named 51572_Seq_Listing.TXT, and is 5,814 bytes in size.

TECHNICAL FIELD

The present invention relates generally to pharmaceutical compositions. In particular, the invention relates to microparticles with adsorbent surfaces, methods for preparing such microparticles, and uses thereof, such as vaccines; additionally, the present invention is directed to adjuvant compositions comprising oil droplet emulsions and uses thereof, such as vaccines. Additionally, the invention relates to compositions comprising biodegradable microparticles and/or microemulsions wherein biologically active agents, such as therapeutic polynucleotides, polypeptides, antigens, and adjuvants, are adsorbed thereto.

BACKGROUND

Particulate carriers have been used in order to achieve controlled, parenteral delivery of therapeutic compounds. Such carriers are designed to maintain the active agent in the delivery system for an extended period of time. Examples of particulate carriers include those derived from polymethyl methacrylate polymers, as well as microparticles derived from poly(lactides) (see, e.g., U.S. Pat. No. 3,773,919), poly (lactide-co-glycolides), known as PLG (see, e.g., U.S. Pat. No. 4,767,628) and polyethylene glycol, known as PEG (see, e.g., U.S. Pat. No. 5,648,095). Polymethyl methacrylate polymers are nondegradable while PLG particles biodegrade by random nonenzymatic hydrolysis of ester bonds to lactic and glycolic acids which are excreted along normal metabolic pathways.

For example, U.S. Pat. No. 5,648,095 describes the use of microspheres with encapsulated pharmaceuticals as drug delivery systems for nasal, oral, pulmonary and oral delivery. Slow-release formulations containing various polypeptide growth factors have also been described. See, e.g., International Publication No. WO 94/12158, U.S. Pat. No. 5,134,122 and International Publication No. WO 96/37216.

Fattal et al., Journal of Controlled Release 53:137-143 (1998) describes nanoparticles prepared from polyalkylcyanoacrylates (PACA) having adsorbed oligonucleotides.

Particulate carriers, such as microparticles, have also been used with adsorbed or entrapped antigens in attempts to elicit adequate immune responses. Such carriers present multiple copies of a selected antigen to the immune system and promote trapping and retention of antigens in local lymph nodes. The particles can be phagocytosed by macrophages and can enhance antigen presentation through cytokine release. For example, commonly owned, co-pending application Ser. No. 09/015,652, filed Jan. 29, 1998, describes the use of antigen-adsorbed and antigen-encapsulated microparticles to stimulate cell-mediated immunological responses, as well as methods of making the microparticles.

In commonly owned provisional Patent Application 60/036,316, for example, a method of forming microparticles is disclosed which comprises combining a polymer with an organic solvent, then adding an emulsion stabilizer, such as polyvinyl alcohol (PVA), then evaporating the organic solvent, thereby forming microparticles. The surface of the microparticles comprises the polymer and the stabilizer. Macromolecules such as DNA, polypeptides, and antigens may then be adsorbed on those surfaces.

While antigen-adsorbed PLG microparticles offer significant advantages over other more toxic systems, adsorption of biologically active agents to the microparticle surface can be problematic. For example, it is often difficult or impossible to adsorb charged or bulky biologically active agents, such as polynucleotides, large polypeptides, and the like, to the microparticle surface. Thus, there is a continued need for flexible delivery systems for such agents and, particularly for drugs that are highly sensitive and difficult to formulate.

Adjuvants are compounds which are capable of potentiating an immune response to antigens. Adjuvants can potentiate both humoral and cellular immunity. However, it is preferable for certain pathogens to stimulate cellular immunity and, indeed, Th1 cells. Presently used adjuvants do not adequately induce Th1 cell responses, and/or have deleterious side effects.

Currently, the only adjuvants approved for human use in the United States are aluminum salts (alum). These adjuvants have been useful for some vaccines including hepatitis B, diphtheria, polio, rabies, and influenza, but may not be useful for others, especially if stimulation of cell-mediated immunity is required for protection. For example, reports indicate that alum failed to improve the effectiveness of whooping cough and typhoid vaccines and provided only a slight effect with adenovirus vaccines. Additionally, problems such as, induction of granulomas at the injection site and lot-to-lot variation of alum preparations have been experienced.

Complete Freund's adjuvant (CFA) is a powerful immunostimulatory agent that has been used successfully with many antigens on an experimental basis. CFA is comprised of three components: a mineral oil, an emulsifying agent such as Arlacel A, and killed mycobacteria such as *Mycobacterium tuberculosis*. Aqueous antigen solutions are mixed with these components to create a water-in-oil emulsion. CFA causes severe side effects, however, including pain, abscess formation, and fever, which prevent its use in either human or veterinary vaccines. The side effects are primarily due to the host's reactions to the mycobacterial component of CFA. Incomplete Freund's adjuvant (IFA) is similar to CFA without the bacterial component. While not approved for use in the United States, IFA has been useful for several types of vaccines in other countries. IFA has been used successfully in humans with influenza and polio vaccines and with several animal vaccines including rabies, canine distemper, and foot-and-mouth disease. Experiments have shown, however, that both the oil and emulsifier used in IFA can cause tumors in mice, indicating that an alternative adjuvant would be a better choice for human use.

Muramyl dipeptide (MDP) represents the minimal unit of the mycobacterial cell wall complex that generates the adjuvant activity observed with CFA. Ellouz et al., *Biochem. Biophys. Res. Comm.*, 1974, 59, 1317. Many synthetic analogs of MDP have been generated that exhibit a wide range of adjuvant potency and side effects. Chedid et al., *Prog. Allergy*, 1978, 25, 63. Three analogs of MDP—threonyl derivatives of MDP (Byars et al., *Vaccine*, 1987, 5, 223); n-butyl derivatives of MDP (Chedid et al., *Infect. Immun.*, 1982, 35, 417); and lipophilic derivatives of muramyl tripeptide (Gisler et al., *Immunomodulations of Microbial Products and Related Synthetic Compounds*, Y. Yamamura and S. Kotani, Eds., Excerpta Medica, Amsterdam, p. 167)—have been shown to stimulate humoral and cell-mediated immunity and exhibit low levels of toxicity. Another derivative of MDP, N-acetyl-muramyl-L-alanyl-D-isoglutaminyl-L-alanine-2-[1,2-di-palmitoyl-sn-glycero-3-3(hydroxyphosphoryloxy)]ethylamide (MTP-PE) is lipophilic. MTP-PE has phospholipid tails that allow association of the hydrophobic portion of the molecule with a lipid environment while the muramyl peptide portion associates with the aqueous environment. Thus, MTP-PE itself can act as an emulsifying agent to generate stable oil in water emulsions.

Levamisole and isoprinosine are other synthetic adjuvants that increase host immunity. Levamisole is the levo isomer of tetramisole and potentiates humoral and cellular immunity through a T cell-dependent mechanism. Isoprinosine, a complex containing inosine, the purine precursor of adenosine and guanosine, promotes T cell mitogenesis. Tuftsin, a 4 amino acid peptide (Thr-Lys-Pro-Arg) homologous to a sequence in the immunoglobulin (Ig) heavy chain, primarily stimulates macrophages.

Microparticles prepared from the biodegradable and biocompatible polymers, known as the poly(lactide-co-glycolides) (PLG), have been demonstrated to be effective vehicles for a number of antigens. In addition, PLG microparticles can control the rate of release of entrapped antigens and, thus, offer potential for single-dose vaccines. Moreover, administration of biodegradable polymers with entrapped antigens have been demonstrated in a range of animal models to induce potent immune responses. O'Hagan et al., *Advanced Drug Deliv. Rev.*, 1998, 32, 225-246 and Singh et al., *Advanced Drug Deliv. Rev.*, 1998, 34, 285-304, the disclosures of which are incorporated herein by reference in their entirety.

An emulsion comprising squalene, sorbitan trioleate (Span85™), and polysorbate 80 (Tween 80™) microfluidized to provide uniformly sized microdroplets, i.e. MF59, has also been shown to induce potent immune responses. MF59 formulations have been shown to induce antibody titers 5->100 times greater than those obtained with aluminum salt adjuvants. MF59 has been demonstrated to enhance the immune response to antigens from numerous sources including, for example, herpes simplex virus (HSV), human immunodeficiency virus (HIV), influenza virus, hepatitis C virus (HCV), cytomegalovirus (CMV), hepatitis B virus (HBV), human papillomavirus (HPV), and malaria. Ott et al., *Vaccine Design: The Subunit And Adjuvant Approach*, 1995, M. F. Powell and M. J. Newman, Eds., Plenum Press, New York, p. 277-296; Singh et al., *Vaccine*, 1998, 16, 1822-1827; Ott et al., *Vaccine*, 1995, 13, 1557-1562; O'Hagan et al., *Mol. Medicine Today*, 1997, February, 69-75; and Traquina et al., *J. Infect. Dis.*, 1996, 174, 1168-75, the disclosures of which are incorporated herein by reference in their entirety. MF59 adjuvant improves the immunogenicity of subunit antigens while maintaining the safety and tolerability profile of alum adjuvant. Van Nest et al., *Vaccines* 92, 1992, Cold Spring Harbor Laboratory Press, 57-62 and Valensi et al., *J. Immunol.*, 1994, 153, 4029-39, the disclosures of which are incorporated herein by reference in their entirety. MF59 is further described in co-pending U.S. application Ser. No. 08/434, 512, filed May 4, 1995, which is assigned to the assignee of the present invention, the disclosure of which is incorporated herein by reference in its entirety. In animal studies, MF59 has not been found to be genotoxic, teratogenic, nor does it cause sensitization. The mechanism of action of MF59 appears to be dependent upon the generation of a strong CD4+ T cell, i.e., a Th2 cell response. MF59 adjuvants, however, elicit little, if any, Th1 responses, or cytotoxic T lymphocyte (CTL) responses.

Oligonucleotides comprising CpG motifs mixed with antigens have been demonstrated to induce strong Th1 immune responses. Roman et al., *Nat. Med.*, 1997, 3, 849-854; Weiner et al., *Proc. Natl. Acad. Sci. USA*, 1997, 94, 10833-10837; Davis et al., *J. Immunol.*, 1998, 160, 870-876; Chu et al., *J. Exp. Med.*, 1997, 186, 1623-1631; Lipford et al., *Eur. J. Immunol.*, 1997, 27, 2340-2344; and Moldoveanu et al., *Vaccine*, 1988, 16, 1216-1224, the disclosures of which are incorporated herein by reference in their entirety. Unmethylated CpG dinucleotides are relatively common in bacterial DNA, but are underrepresented and methylated in vertebrate DNA. Bird, *Trends Genet.*, 1987, 3, 342-347. Bacterial DNA or synthetic oligonucleotides containing unmethylated CpG motifs are also known to induce immune responses including, for example, B cell proliferation, interleukin-6 and immunoglobulin secretion, and apoptosis resistance. Krieg et al., *Nature*, 1995, 374, 546-549; Klinman et al., *Proc. Natl. Acad. Sci. USA*, 1996, 93, 2879-2883; Ballas et al., *J. Immunol.*, 1996, 157, 1840-1845; Cowdery et al., *J. Immunol.*, 1996, 156, 4570-4575; Halpern et al., *Cell. Immunol.*, 1996, 167, 72-78; Yamamoto et al., *Jpn. J. Cancer Res.*, 1988, 79, 866-873; Stacey et al., *J. Immunol.*, 1996, 157, 2116-2122; Messina et al., *J. Immunol.*, 1991, 147, 1759-1764; Yi et al., *J. Immunol.*, 1996, 157, 4918-4925; Yi et al., *J. Immunol.*, 1996, 157, 5394-5402; Yi et al., *J. Immunol.*, 1998, 160, 4755-4761; and Yi et al., *J. Immunol.*, 1998, 160, 5898-5906; PCT Publication WO 96/02555; PCT Publication WO 98/16247; PCT Publication WO 98/18810; PCT Publication WO 98/40100; PCT Publication WO 98/55495; PCT Publication WO 98/37919; and PCT Publication WO 98/52581, the disclosures of which are incorporated herein by reference in their entirety.

Monophosphoryl lipid A (MPL) is known to those skilled in the art to induce a Th1 lymphocyte response. Ullrich et al., Monophosphoryl Lipid A as an Adjuvant in Vaccine Design The Subunit and Adjuvant Approach, Powell and Newman, Eds., 1995, Plenum Press, New York, p. 495-523.

It has also been shown that cationic lipid-based emulsions may be used as gene carriers. See, e.g., Yi et al., *Cationic Lipid Emulsion; a Novel Non-Viral, and Non-Liposomal Gene Delivery System*, Proc. Int'l. Symp. Control. Rel. Bioact. Mater., 24:653-654 (1997); Kim et al., *In Vivo Gene Transfer Using Cationic Lipid Emulsion-Mediated Gene Delivery System by Intra Nasal Administration*, Proc. Int'l. Symp. Control. Rel. Bioact. Mater., 25:344-345 (1998); Kim et al., *In Vitro and In Vivo Gene Delivery Using Cationic Lipid Emulsion*, Proc. Int'l. Symp. Control. Rel. Bioact. Mater., 26, #5438 (1999).

An adjuvant which results in the increase of a Th1 cell response which can be used for prophylactic and therapeutic treatment is, thus, still desired. Such a response would be helpful in treatment of, for example, viral infections as well as for immunizing individuals susceptible to viral infections.

SUMMARY OF THE INVENTION

The inventors herein have invented a method of forming microparticles with adsorbent surfaces capable of adsorbing a wide variety of macromolecules. The microparticles are comprised of both a polymer and a detergent. The microparticles of the present invention adsorb such macromolecules more efficiently than other microparticles currently available.

The microparticles are derived from a polymer, such as a poly($\alpha$-hydroxy acid), a polyhydroxy butyric acid, a polycaprolactone, a polyorthoester, a polyanhydride, a PACA, a polycyanoacrylate, and the like, and are formed with detergents, such as cationic, anionic, or nonionic detergents, which detergents may be used in combination. Additionally, the inventors have discovered that these microparticles yield improved adsorption of viral antigens, and provide for superior immune responses, as compared to microparticles formed by a process using only PVA. While microparticles made using only PVA may adsorb some macromolecules, the microparticles of the present invention using other detergents alone, in combination, or in combination with PVA, adsorb a wide variety of macromolecules. Accordingly, then, the invention is primarily directed to such microparticles, as well as to processes for producing the same and methods of using the microparticles.

In one embodiment, the invention is directed to a microparticle with an adsorbent surface, wherein the microparticle comprises a polymer selected from the group consisting of a poly($\alpha$-hydroxy acid), a polyhydroxy butyric acid, a polycaprolactone, a polyorthoester, a polyanhydride, and a polycyanoacrylate.

In another embodiment, the invention is directed to such microparticles which further comprise a selected macromolecule adsorbed on the microparticle's surface, such as a pharmaceutical, a polynucleotide, a polypeptide, a protein, a hormone, an enzyme, a transcription or translation mediator, an intermediate in a metabolic pathway, an immunomodulator, an antigen, an adjuvant, or combinations thereof, and the like.

In another embodiment, the invention is directed to a microparticle composition comprising a selected macromolecule adsorbed to a microparticle of the invention and a pharmaceutically acceptable excipient.

In another embodiment, the invention is directed to a method of producing a microparticle having an adsorbent surface, the method comprising:
(a) combining a polymer solution comprising a polymer selected from the group consisting of a poly($\alpha$-hydroxy acid), a polyhydroxy butyric acid, a polycaprolactone, a polyorthoester, a polyanhydride, and a polycyanoacrylate, wherein the polymer is present at a concentration of about 1% to about 30% in an organic solvent;
and an anionic, cationic, or nonionic detergent to the polymer solution, wherein the detergent is present at a ratio of 0.001 to 10 (w/w) detergent to polymer, to form a polymer/detergent mixture;
(b) dispersing the polymer/detergent mixture;
(c) removing the organic solvent; and
(d) recovering the microparticle.
Preferably, the polymer/detergent mixture is emulsified to form an emulsion prior to removing the organic solvent.

In another embodiment, the invention is directed to a microparticle produced by the above described methods.

In another embodiment, the invention is directed to a method of producing a microparticle with an adsorbed macromolecule comprising:
(a) combining a polymer solution comprising poly(D,L-lactide-co-glycolide), wherein the polymer is present at a concentration of about 3% to about 10% in an organic solvent;
and an anionic, cationic, or nonionic detergent, wherein the detergent is present at a ratio of 0.001 to 10 (w/w) detergent to polymer, to form a polymer/detergent mixture;
(b) dispersing the polymer/detergent mixture;
(c) removing the organic solvent from the emulsion;
(d) recovering the microparticle; and
(e) adsorbing a macromolecule to the surface of the microparticle, wherein the macromolecule is selected from the group consisting of a pharmaceutical, a polynucleotide, a polypeptide, a hormone, an enzyme, a transcription or translation mediator, an intermediate in a metabolic pathway, an immunomodulator, an antigen, an adjuvant, and combinations thereof. Preferably, the polymer/detergent mixture is emulsified to form an emulsion prior to removing the organic solvent. In another embodiment, the invention is directed to a microparticle with an adsorbed macromolecule produced by the above described method.

In another embodiment, the invention is directed to a method of producing an adsorbent microparticle composition comprising combining an adsorbent microparticle having a macromolecule adsorbed on the surface thereof and a pharmaceutically acceptable excipient.

In yet another embodiment, the invention is directed to a method of delivering a macromolecule to a vertebrate subject which comprises administering to a vertebrate subject the composition above.

In an additional embodiment, the invention is directed to a method for eliciting a cellular immune response in a vertebrate subject comprising administering to a vertebrate subject a therapeutically effective amount of a selected macromolecule adsorbed to a microparticle of the invention.

In another embodiment, the invention is directed to a method of immunization which comprises administering to a vertebrate subject a therapeutically effective amount of the microparticle composition above. The composition may optionally contain unbound macromolecules, and also may optionally contain adjuvants, including aluminum salts such as aluminum phosphate.

In a preferred embodiment, the microparticles are formed from a poly($\alpha$-hydroxy acid); more preferably, a poly(D,L-lactide-co-glycolide); and most preferably, a poly(D,L-lactide-co-glycolide).

In another embodiment of the present invention, a microparticle preparation comprises submicron emulsions with ionic surfactants. MF59 or others may be used as the base particle, while ionic surfactants may include, but are not limited to, Dioleoyl-3-Trimethylammonium-Propane (DOTAP), Dioleoyl-sn-Glycero-3-Ethylphosphocholine (DEPC) and dioleoyl-phosphatidic acid (DPA), each of which are soluble in squalene.

Each of the nonexhaustive previously described adsorbent microparticles may optionally also have macromolecules entrapped within them.

The present invention is also directed to microemulsions which comprise an oil droplet emulsion formulated with an ionic detergent. Such compositions readily adsorb macromolecules such as DNA, protein, and other antigenic molecules. Adjuvant compositions may comprise an oligonucleotide comprising at least one CpG motif. The adjuvant composition can also comprise an optional component which results in a positively charged emulsion. The oil droplet emulsion preferably comprises a metabolizable oil and an emulsifying agent which are preferably present in the form of an oil-in-water emulsion having oil droplets substantially all of which are less than 1 micron in diameter. Preferably, the composition exists in the absence of any polyoxypropylene-polyoxyethylene block copolymer. The oil is preferably an animal oil, an unsaturated hydrocarbon, a terpenoid such as, for example, squalene, or a vegetable oil. The composition preferably comprises 0.5 to 20% by volume of the oil in an aqueous medium. The emulsifying agent preferably comprises a non-ionic detergent such as a polyoxyethylene sorbitan mono-, di-, or triester or a sorbitan mono-, di-, or triether. Preferably, the composition comprises about 0.01 to about 0.5% by weight of the emulsifying agent. The oligonucleotide preferably comprises at least one phosphorothioate bond or peptide nucleic acid bond. In preferred embodiments of the invention, the oligonucleotide comprises a nucleotide sequence selected from the group consisting of SEQ ID NOs: 1-28. In other preferred embodiments of the invention, the oligonucleotide comprises a CpG motif flanked by two purines immediately 5' to the motif and two pyrimidines immediately 3' to the motif. In other preferred embodiments of the invention, the oligonucleotide comprises a nucleotide sequence selected from the group consisting of SEQ ID NOs: 19-28. Most preferred is SEQ ID NO:28. In some preferred embodiments of the invention, the adjuvant composition further comprises a separate immunostimulating agent which is preferably selected from the group consisting of alum, a bacterial cell wall component, and muramyl peptide. The adjuvant composition can be in the form of a microparticle.

The present invention is also directed to immunogenic compositions comprising an immunostimulating amount of an antigenic substance, and an immunostimulating amount of an adjuvant composition described herein. Preferably, the antigenic substance is selected from the group consisting of a protein, protein-polysaccharide, protein-lipopolysaccharide, polysaccharide, and lipopolysaccharide. In some embodiments of the invention, the immunogenic composition comprises a CpG oligonucleotide in combination with an antigenic substance adsorbed to poly(lactide-co-glycolide) microparticles. The adsorbed antigenic substance is preferably a recombinant protein. In preferred embodiments of the invention, the antigenic substance is from a virus such as, for example, hepatitis C virus (HCV), hepatitis B virus (HBV), herpes simplex virus (HSV), human immunodeficiency virus (HIV), cytomegalovirus (CMV), influenza virus (flu), and rabies virus. Preferably, the antigenic substance is selected from the group consisting of HSV glycoprotein gD, HIV glycoprotein gp120, and HIV p55 gag. In other preferred embodiments of the invention, the antigenic substance is from a bacterium such as, for example, cholera, diphtheria, tetanus, pertussis, *Neisseria meningitidis, Neisseria gonorrhoeae, Helicobacter pylori*, and *Haemophilus influenza*. In other preferred embodiments of the invention, the antigenic substance is from a parasite such as, for example, a malaria parasite.

The present invention is also directed to methods of stimulating an immune response in a host animal comprising administering to the animal an immunogenic composition described herein in an amount effective to induce an immune response. The host animal is preferably a mammal, more preferably a human.

The present invention is also directed to methods of immunizing a host animal against a viral, bacterial, or parasitic infection comprising administering to the animal an immunogenic composition described herein in an amount effective to induce a protective response. The host animal is preferably a mammal, more preferably a human.

The present invention is also directed to methods of increasing a Th1 immune response in a host animal comprising administering to the animal an immunogenic composition described herein in an amount effective to induce a Th1 immune response. The host animal is preferably a mammal, more preferably a human.

These and other embodiments of the present invention will readily occur to those of ordinary skill in the art in view of the disclosure herein.

BRIEF DESCRIPTION OF THE DRAWINGS

FIG. 3 is a chart showing representative results of serum anti-p55 IgG titer upon immunization with a preferred emulsion adjuvant.

FIG. 4 is a chart showing representative results of lysis of targets by CTL upon immunization with a preferred emulsion adjuvant.

DETAILED DESCRIPTION OF THE INVENTION

Figure 1:
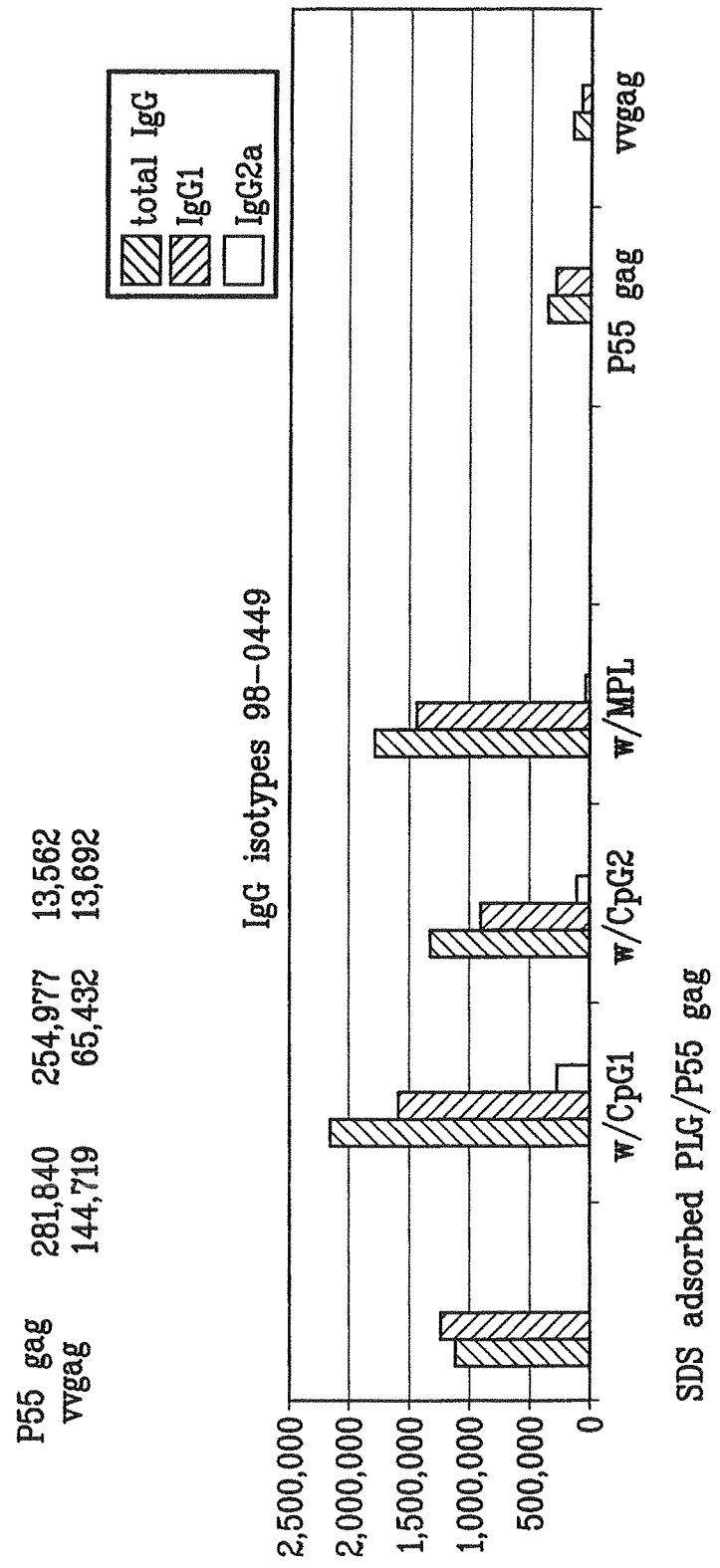
FIG. 1 is a bar graph showing typical results of immunoglobulin isotypes generated by preferred immunogenic compositions comprising PLG microparticles according to the invention.

The present invention is based upon the surprising discoveries that microparticles with adsorbed macromolecules elicit improved immune responses, and that an adjuvant containing a combination of a CpG oligonucleotide and a metabolizable oil or biodegradable polymer increases immune responses. Additionally, the combination of microparticles with adsorbed macromolecules and oil emulsion adjuvants is useful for eliciting a strong immune responses.

The practice of the present invention will employ, unless otherwise indicated, conventional methods of chemistry, polymer chemistry, biochemistry, molecular biology, immunology and pharmacology, within the skill of the art. Such techniques are explained fully in the literature. See, e.g., *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); *Handbook of Experimental Immunology*, Vols. I-IV (D. M. Weir and C. C. Blackwell, eds., 1986, Blackwell Scientific Publications); Sambrook, et al., *Molecular Cloning: A Laboratory Manual* (2nd Edition, 1989); *Handbook of Surface and Colloidal Chemistry* (Birdi, K. S., ed, CRC Press, 1997) and *Seymour/Carraher's Polymer Chemistry* (4th edition, Marcel Dekker Inc., 1996).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise. Thus, for example, the term "microparticle" refers to one or more microparticles, and the like.

A. DEFINITIONS

In describing the present invention, the following terms will be employed, and are intended to be defined as indicated below.

The term "microparticle" as used herein, refers to a particle of about 10 nm to about 150 μm in diameter, more preferably about 200 nm to about 30 μm in diameter, and most preferably about 500 nm to about 10 μm in diameter. Preferably, the microparticle will be of a diameter that permits parenteral or mucosal administration without occluding needles and capillaries. Microparticle size is readily determined by techniques well known in the art, such as photon correlation spectroscopy, laser diffractometry and/or scanning electron microscopy. The term "particle" may also be used to denote a microparticle as defined herein.

Microparticles for use herein will be formed from materials that are sterilizable, non-toxic and biodegradable. Such materials include, without limitation, poly(α-hydroxy acid), polyhydroxybutyric acid, polycaprolactone, polyorthoester, polyanhydride, PACA, and polycyanoacrylate. Preferably, microparticles for use with the present invention are derived from a poly(α-hydroxy acid), in particular, from a poly(lactide) ("PLA") or a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered macromolecule. These parameters are discussed more fully below.

The term "detergent" as used herein includes surfactants and emulsion stabilizers. Anionic detergents include, but are not limited to, SDS, SLS, DSS (disulfosuccinate), sulphated fatty alcohols, and the like. Cationic detergents include, but are not limited to, cetrimide (CTAB), benzalkonium chloride, DDA (dimethyl dioctodecyl ammonium bromide), DOTAP, and the like. Nonionic detergents include, but are not limited to, sorbitan esters, polysorbates, polyoxyethylated glycol monoethers, polyoxyethylated alkyl phenols, poloxamers, and the like.

The term "net positive charge" as used herein, means that the charge on the surface of the microparticle is more positive than the charge on the surface of a corresponding microparticle made using PVA. Likewise, the term "net negative charge" as used herein, means that the charge on the surface of the microparticle is more negative than the charge on the surface of a corresponding microparticle made using PVA. Net charge can be assessed by comparing the zeta potential (also known as electrokinetic potential) of the microparticle made using a cationic or anionic detergent with a corresponding microparticle made using PVA. Thus, a microparticle surface having a "net positive charge" will have a zeta potential greater than the zeta potential of the surface of a microparticle made using PVA and a microparticle having a "net negative charge" will have a zeta potential less than the zeta potential of the surface of a microparticle made using PVA. As is apparent, the net charges for the microparticles of the invention are calculated relative to the zeta potential of a corresponding PVA microparticle.

The term "zeta potential" as used herein, refers to the electrical potential that exists across the interface of all solids and liquids, i.e., the potential across the diffuse layer of ions surrounding a charged colloidal particle. Zeta potential can be calculated from electrophoretic mobilities, i.e., the rates at which colloidal particles travel between charged electrodes placed in contact with the substance to be measured, using techniques well known in the art.

The term "macromolecule" as used herein refers to, without limitation, a pharmaceutical, a polynucleotide, a polypeptide, a hormone, an enzyme, a transcription or translation mediator, an intermediate in a metabolic pathway, an immunomodulator, an antigen, an adjuvant, or combinations thereof. Particular macromolecules for use with the present invention are described in more detail below.

The term "pharmaceutical" refers to biologically active compounds such as antibiotics, antiviral agents, growth factors, hormones, and the like, discussed in more detail below.

A "polynucleotide" is a nucleic acid molecule which encodes a biologically active (e.g., immunogenic or therapeutic) protein or polypeptide. Depending on the nature of the polypeptide encoded by the polynucleotide, a polynucleotide can include as little as 10 nucleotides, e.g., where the polynucleotide encodes an antigen. Furthermore, a "polynucleotide" can include both double- and single-stranded sequences and refers to, but is not limited to, cDNA from viral, procaryotic or eucaryotic mRNA, genomic RNA and DNA sequences from viral (e.g. RNA and DNA viruses and retroviruses) or procaryotic DNA, and especially synthetic DNA sequences. The term also captures sequences that include any of the known base analogs of DNA and RNA, and includes modifications, such as deletions, additions and substitutions (generally conservative in nature), to the native sequence, so long as the nucleic acid molecule encodes a therapeutic or antigenic protein. These modifications may be deliberate, as through site-directed mutagenesis, or may be accidental, such as through mutations of hosts which produce the antigens.

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include modifications, such as deletions, additions and substitutions (generally conservative in nature), to the native sequence, so long as the protein maintains the ability to elicit an immunological response or have a therapeutic effect on a subject to which the protein is administered.

By "antigen" is meant a molecule which contains one or more epitopes capable of stimulating a host's immune system to make a cellular antigen-specific immune response when the antigen is presented in accordance with the present invention, or a humoral antibody response. An antigen may be capable of eliciting a cellular or humoral response by itself or when present in combination with another molecule. Normally, an epitope will include between about 3-15, generally about 5-15, amino acids. Epitopes of a given protein can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra.

The term "antigen" as used herein denotes both subunit antigens, i.e., antigens which are separate and discrete from a whole organism with which the antigen is associated in nature, as well as killed, attenuated or inactivated bacteria, viruses, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses a therapeutic or immunogenic protein, or antigenic determinant in vivo, such as in gene therapy and nucleic acid immunization applications, is also included in the definition of antigen herein.

Further, for purposes of the present invention, antigens can be derived from any of several known viruses, bacteria, parasites and fungi, as well as any of the various tumor antigens. Furthermore, for purposes of the present invention, an "antigen" refers to a protein which includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts which produce the antigens.

An "immunological response" to an antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition, such as an immunogenic composition, or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen or composition to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376; and the examples below.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

A composition which contains a selected antigen adsorbed to a microparticle, displays "enhanced immunogenicity" when it possesses a greater capacity to elicit an immune response than the immune response elicited by an equivalent amount of the antigen when delivered without association with the microparticle. Thus, a composition may display "enhanced immunogenicity" because the antigen is more strongly immunogenic by virtue of adsorption to the microparticle, or because a lower dose of antigen is necessary to achieve an immune response in the subject to which it is administered. Such enhanced immunogenicity can be determined by administering the microparticle/antigen composition, and antigen controls to animals and comparing antibody titers against the two using standard assays such as radioimmunoassay and ELISAs, well known in the art.

The terms "effective amount" or "pharmaceutically effective amount" of a macromolecule/microparticle, as provided herein, refer to a nontoxic but sufficient amount of the macromolecule/microparticle to provide the desired response, such as an immunological response, and corresponding therapeutic effect, or in the case of delivery of a therapeutic protein, an amount sufficient to effect treatment of the subject, as defined below. As will be pointed out below, the exact amount required will vary from subject to subject, depending on the species, age, and general condition of the subject, the severity of the condition being treated, and the particular macromolecule of interest, mode of administration, and the like. An appropriate "effective" amount in any individual case may be determined by one of ordinary skill in the art using routine experimentation.

By "vertebrate subject" is meant any member of the subphylum cordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds. The term does not denote a particular age. Thus, both adult and newborn animals are intended to be covered.

By "pharmaceutically acceptable" or "pharmacologically acceptable" is meant a material which is not biologically or otherwise undesirable, i.e., the material may be administered to an individual along with the microparticle formulation without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

As used herein, "treatment" refers to any of (i) the prevention of infection or reinfection, as in a traditional vaccine, (ii) the reduction or elimination of symptoms, and (iii) the substantial or complete elimination of the pathogen or disorder in question. Treatment may be effected prophylactically (prior to infection) or therapeutically (following infection).

As used herein, the phrase "nucleic acid" refers to DNA, RNA, or chimeras formed therefrom.

As used herein, the phrase "oligonucleotide comprising at least one CpG motif" refers to a polynucleotide comprising at least one CpG dinucleotide. Oligonucleotides comprising at least one CpG motif can comprise multiple CpG motifs. These oligonucleotide are also known in the art as "CpG oligonucleotides" in the art. As used herein, the phrase "CpG motif" refers to a dinucleotide portion of an oligonucleotide which comprises a cytosine nucleotide followed by a guanosine nucleotide. 5-methylcytosine can also be used in place of cytosine.

As used herein, the phrase "oil droplet emulsion" refers to an emulsion comprising a metabolizable oil and an emulsifying agent.

According to some embodiments of the present invention, compositions and methods are provided which prophylactically and/or therapeutically immunize or treat a host animal against viral, fungal, mycoplasma, bacterial, or protozoan infections, as well as to tumors. The methods of the present invention are useful for conferring prophylactic and/or therapeutic immunity to a mammal, preferably a human. The methods of the present invention can also be practiced on mammals, other than humans, for biomedical research.

B. GENERAL METHODS

1. Microparticles with Adsorbed Macromolecules

The present invention is based on the discovery that the PLA and PLG microparticles of the present invention efficiently adsorb biologically active macromolecules. Further, these microparticles adsorb a greater variety of molecules, including charged and/or bulky macromolecules, more readily than microparticles prepared with PVA. Thus the macromolecule/microparticle of the present invention can be used as a delivery system to deliver the biologically active components in order to treat, prevent and/or diagnose a wide variety of diseases.

The present invention can be used to deliver a wide variety of macromolecules including, but not limited to, pharmaceuticals such as antibiotics and antiviral agents, nonsteroidal antiinflammatory drugs, analgesics, vasodilators, cardiovascular drugs, psychotropics, neuroleptics, antidepressants, antiparkinson drugs, beta blockers, calcium channel blockers, bradykinin inhibitors, ACE-inhibitors, vasodilators, prolactin inhibitors, steroids, hormone antagonists, antihistamines, serotonin antagonists, heparin, chemotherapeutic agents, antineoplastics and growth factors, including but not limited to PDGF, EGF, KGF, IGF-1 and IGF-2, FGF, polynucleotides which encode therapeutic or immunogenic proteins, immunogenic proteins and epitopes thereof for use in vaccines, hormones including peptide hormones such as insulin, proinsulin, growth hormone, GHRH, LHRH, EGF, somatostatin, SNX-111, BNP, insulinotropin, ANP, FSH, LH, PSH and hCG, gonadal steroid hormones (androgens, estrogens and progesterone), thyroid-stimulating hormone, inhibin, cholecystokinin, ACTH, CRF, dynorphins, endorphins, endothelin, fibronectin fragments, galanin, gastrin, insulinotropin, glucagon, GTP-binding protein fragments, guanylin, the leukokinins, magainin, mastoparans, dermaseptin, systemin, neuromedins, neurotensin, pancreastatin, pancreatic polypeptide, substance P, secretin, thymosin, and the like, enzymes, transcription or translation mediators, intermediates in metabolic pathways, immunomodulators, such as any of the various cytokines including interleukin-1, interleukin-2, interleukin-3, interleukin-4, and gamma-interferon, antigens, and adjuvants.

In a preferred embodiment the macromolecule is an antigen. A particular advantage of the present invention is the ability of the microparticles with adsorbed antigen to generate cell-mediated immune responses in a vertebrate subject. The ability of the antigen/microparticles of the present invention to elicit a cell-mediated immune response against a selected antigen provides a powerful tool against infection by a wide variety of pathogens. Accordingly, the antigen/microparticles of the present invention can be incorporated into vaccine compositions.

Thus, in addition to a conventional antibody response, the system herein described can provide for, e.g., the association of the expressed antigens with class I MHC molecules such that an in vivo cellular immune response to the antigen of interest can be mounted which stimulates the production of CTLs to allow for future recognition of the antigen. Furthermore, the methods may elicit an antigen-specific response by helper T-cells. Accordingly, the methods of the present invention will find use with any macromolecule for which cellular and/or humoral immune responses are desired, preferably antigens derived from viral pathogens that may induce antibodies, T-cell helper epitopes and T-cell cytotoxic epitopes. Such antigens include, but are not limited to, those encoded by human and animal viruses and can correspond to either structural or non-structural proteins.

The microparticles of the present invention are particularly useful for immunization against intracellular viruses which normally elicit poor immune responses. For example, the present invention will find use for stimulating an immune response against a wide variety of proteins from the herpesvirus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpesviruses such as HHV6 and HHV7. (See, e.g. Chee et al., *Cytomegaloviruses* (J. K. McDougall, ed., Springer-Verlag 1990) pp. 125-169, for a review of the protein coding content of cytomegalovirus; McGeoch et al., *J. Gen. Virol.* (1988) 69:1531-1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207-211, for the identification of protein coding sequences in an EBV genome; and Davison and Scott, *J. Gen. Virol.* (1986) 67:1759-1816, for a review of VZV.)

Antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NS1) and an N-terminal nucleocapsid protein (termed "core") (see, Houghton et al., *Hepatology* (1991) 14:381-388, for a discussion of HCV proteins, including E1 and E2). Each of these proteins, as well as antigenic fragments thereof, will find use in the present composition and methods.

Similarly, the sequence for the δ-antigen from HDV is known (see, e.g., U.S. Pat. No. 5,378,814) and this antigen can also be conveniently used in the present composition and methods. Additionally, antigens derived from HBV, such as the core antigen, the surface antigen, sAg, as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, will find use herein. See, e.g., "HBV Vaccines—from the laboratory to license: a case study" in Mackett, M. and Williamson, J. D., *Human Vaccines and Vaccination*, pp. 159-176, for a discussion of HBV structure; and U.S. Pat. Nos. 4,722,840, 5,098,704, 5,324,513, incorporated herein by reference in their entireties; Beames et al., *J. Virol.* (1995) 69:6833-6838, Birnbaum et al., *J. Virol.* (1990) 64:3319-3330; and Zhou et al., *J. Virol.* (1991) 65:5457-5464.

Antigens derived from other viruses will also find use in the claimed compositions and methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabdoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); $HIV-1_{CM235}$, $HIV-1_{US4}$; HIV-2; simian immunodeficiency virus (SIV) among others. Additionally, antigens may also be derived from human papillomavirus (HPV) and the tick-borne encephalitis viruses. See, e.g. Virology, 3rd Edition (W. K. Joklik ed. 1988); *Fundamental Virology*, 2nd Edition (B. N. Fields and D. M. Knipe, eds. 1991), for a description of these and other viruses.

More particularly, the gp120 envelope proteins from any of the above HIV isolates, including members of the various genetic subtypes of HIV, are known and reported (see, e.g., Myers et al., Los Alamos Database, Los Alamos National Laboratory, Los Alamos, N. Mex. (1992); Myers et al., *Human Retroviruses and Aids*, 1990, Los Alamos, N. Mex.: Los Alamos National Laboratory; and Modrow et al., *J. Virol.* (1987) 61:570-578, for a comparison of the envelope sequences of a variety of HIV isolates) and antigens derived from any of these isolates will find use in the present methods. Furthermore, the invention is equally applicable to other immunogenic proteins derived from any of the various HIV isolates, including any of the various envelope proteins such as gp160 and gp41, gag antigens such as p24gag and p55gag, as well as proteins derived from the pol region.

Influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* (1990) 179:759-767; Webster et al., "Antigenic variation among type A influenza viruses," p. 127-168. In: P. Palese and D. W. Kingsbury (ed.), *Genetics of influenza viruses*. Springer-Verlag, New York). Thus, proteins derived from any of these isolates can also be used in the compositions and methods described herein.

The compositions and methods described herein will also find use with numerous bacterial antigens, such as those derived from organisms that cause diphtheria, cholera, tuberculosis, tetanus, pertussis, meningitis, and other pathogenic states, including, without limitation, *Bordetella pertussis*, *Neisseria meningitides* (A, B, C, Y), *Neisseria gonorrhoeae*, *Helicobacter pylori*, and *Haemophilus influenza*. *Hemophilus influenza* type B (HIB), *Helicobacter pylori*, and combinations thereof. Examples of antigens from *Neisseria meningitides* B are disclosed in the following co-owned patent applications: PCT/US99/09346; PCT IB98/01665; PCT IB99/00103; and U.S. Provisional Application Ser. Nos. 60/083,758; 60/094,869; 60/098,994; 60/103,749; 60/103,794; 60/103,796; and 60/121,528. Examples of parasitic antigens include those derived from organisms causing malaria and Lyme disease.

It is readily apparent that the subject invention can be used to deliver a wide variety of macromolecules and hence to treat, prevent and/or diagnose a large number of diseases. In an alternative embodiment, the macromolecule/microparticle compositions of the present invention can be used for site-specific targeted delivery. For example, intravenous administration of the macromolecule/microparticle compositions can be used for targeting the lung, liver, spleen, blood circulation, or bone marrow.

The adsorption of macromolecules to the surface of the adsorbent microparticles (or to microemulsions of the present invention) occurs via any bonding-interaction mechanism, including, but not limited to, ionic bonding, hydrogen bonding, covalent bonding, Van der Waals bonding, and bonding through hydrophilic/hydrophobic interactions. Those of ordinary skill in the art may readily select detergents appropriate for the type of macromolecule to be adsorbed For example, microparticles manufactured in the presence of charged detergents, such as anionic or cationic detergents, may yield microparticles with a surface having a net negative or a net positive charge, which can adsorb a wide variety of molecules. For example, microparticles manufactured with anionic detergents, such as sodium dodecyl sulfate (SDS), i.e. SDS-PLG microparticles, adsorb positively charged antigens, such as proteins. Similarly, microparticles manufactured with cationic detergents, such as hexadecyltrimethylammonium bromide (CTAB), i.e. CTAB-PLG microparticles, adsorb negatively charged macromolecules, such as DNA. Where the macromolecules to be adsorbed have regions of positive and negative charge, either cationic or anionic detergents may be appropriate.

Biodegradable polymers for manufacturing microparticles for use with the present invention are readily commercially available from, e.g., Boehringer Ingelheim, Germany and Birmingham Polymers, Inc., Birmingham, Ala. For example, useful polymers for forming the microparticles herein include those derived from polyhydroxybutyric acid; polycaprolactone; polyorthoester; polyanhydride; as well as a poly(α-hydroxy acid), such as poly(L-lactide), poly(D,L-lactide) (both known as APLA" herein), poly(hydroxybutyrate), copolymers of D,L-lactide and glycolide, such as poly(D,L-lactide-co-glycolide) (designated as "PLG" or "PLGA" herein) or a copolymer of D,L-lactide and caprolactone. Particularly preferred polymers for use herein are PLA and PLG polymers. These polymers are available in a variety of molecular weights, and the appropriate molecular weight for a given use is readily determined by one of skill in the art. Thus, e.g., for PLA, a suitable molecular weight will be on the order of about 2000 to 5000. For PLG, suitable molecular weights will generally range from about 10,000 to about 200,000, preferably about 15,000 to about 150,000, and most preferably about 50,000 to about 100,000.

If a copolymer such as PLG is used to form the microparticles, a variety of lactide:glycolide ratios will find use herein and the ratio is largely a matter of choice, depending in part on the coadministered macromolecule and the rate of degradation desired. For example, a 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component. It is readily apparent that a suitable ratio of lactide:glycolide is easily determined by one of skill in the art based on the nature of the antigen and disorder in question. Moreover, in embodiments of the present invention wherein antigen or adjuvants are entrapped within microparticles, mixtures of microparticles with varying lactide:glycolide ratios will find use herein in order to achieve the desired release kinetics for a given macromolecule and to provide for both a primary and secondary immune response. Degradation rate of the microparticles of the present invention can also be controlled by such factors as polymer molecular weight and polymer crystallinity. PLG copolymers with varying lactide:glycolide ratios and molecular weights are readily available commercially from a number of sources including from Boehringer Ingelheim, Germany and Birmingham Polymers, Inc., Birmingham, Ala. These polymers can also be synthesized by simple polycondensation of the lactic acid component using techniques well known in the art, such as described in Tabata et al., *J. Biomed. Mater. Res.* (1988) 22:837-858.

The macromolecule/microparticles are prepared using any of several methods well known in the art. For example, double emulsion/solvent evaporation techniques, such as those described in U.S. Pat. No. 3,523,907 and Ogawa et al., *Chem. Pharm. Bull.* (1988) 36:1095-1103, can be used herein to make the microparticles. These techniques involve the formation of a primary emulsion consisting of droplets of polymer solution, which is subsequently mixed with a continuous aqueous phase containing a particle stabilizer/surfactant.

Alternatively, a water-in-oil-in-water (w/o/w) solvent evaporation system can be used to form the microparticles, as described by O'Hagan et al., *Vaccine* (1993) 11:965-969 and Jeffery et al., *Pharm. Res.* (1993) 10:362. In this technique, the particular polymer is combined with an organic solvent, such as ethyl acetate, dimethylchloride (also called methylene chloride and dichloromethane), acetonitrile, acetone, chloroform, and the like. The polymer will be provided in about a 1-30%, preferably about a 2-15%, more preferably about a 3-10% and most preferably, about a 4% solution, in organic solvent. The polymer solution is emulsified using e.g., an homogenizer. The emulsion is then optionally combined with a larger volume of an aqueous solution of an emulsion stabilizer such as polyvinyl alcohol (PVA), polyvinyl pyrrolidone, and a cationic, anionic, or nonionic detergent. The emulsion may be combined with more than one emulsion stabilizer and/or detergent, e.g., a combination of PVA and a detergent. Certain macromolecules may adsorb more readily to microparticles having a combination of stabilizers and/or detergents. Where an emulsion stabilizer is used, it is typically provided in about a 2-15% solution, more typically about a 4-10% solution. Generally, a weight to weight detergent to polymer ratio in the range of from about 0.00001:1 to about 0.1:1 will be used, more preferably from about 0.0001:1 to about 0.01:1, more preferably from about 0.001:1 to about 0.01:1, and even more preferably from about 0.005:1 to about 0.01:1. The mixture is then homogenized to produce a stable w/o/w double emulsion. Organic solvents are then evaporated.

The formulation parameters can be manipulated to allow the preparation of small microparticles on the order of 0.05 µm (50 nm) to larger microparticles 50 µm or even larger. See, e.g., Jeffery et al., *Pharm. Res.* (1993) 10:362-368; McGee et al., *J. Microencap.* (1996). For example, reduced agitation results in larger microparticles, as does an increase in internal phase volume. Small particles are produced by low aqueous phase volumes with high concentrations of emulsion stabilizers.

Microparticles can also be formed using spray-drying and coacervation as described in, e.g., Thomasin et al., *J. Controlled Release* (1996) 41:131; U.S. Pat. No. 2,800,457; Masters, K. (1976) *Spray Drying* 2nd Ed. Wiley, New York; air-suspension coating techniques, such as pan coating and Wurster coating, as described by Hall et al., (1980) The "Wurster Process" in *Controlled Release Technologies: Methods, Theory, and Applications* (A. F. Kydonieus, ed.), Vol. 2, pp. 133-154 CRC Press, Boca Raton, Fla. and Deasy, P. B., *Crit. Rev. Ther. Drug Carrier Syst.* (1988) S(2):99-139; and ionic gelation as described by, e.g., Lim et al., *Science* (1980) 210:908-910.

Particle size can be determined by, e.g., laser light scattering, using for example, a spectrometer incorporating a helium-neon laser. Generally, particle size is determined at room temperature and involves multiple analyses of the sample in question (e.g., 5-10 times) to yield an average value for the particle diameter. Particle size is also readily determined using scanning electron microscopy (SEM).

An alternative embodiment of the present invention is a microparticle preparation comprising submicron emulsions with ionic surfactants. MF59 or others may be used as the base particle, while ionic surfactants may include, but are not limited to, Dioleoyl-3-Trimethylammonium-Propane (DOTAP), Dioleoyl-sn-Glycero-3-Ethylphosphocholine (DEPC) and dioleoyl-phosphatidic acid (DPA), each of which are soluble in squalene. Prototypic ionic emulsions may be formulated by dissolving each of the detergents in squalene/10% Span 85 at concentrations ranging from 4-52 mg/ml squalene. The squalene/surfactant mixtures may be emulsified with 0.5% Tween 80/$H_2O$ at 5 ml squalene/100 ml $H_2O$. A pre-emulsion may be formed by homogenization with a Silverson homogenizer (5 minutes, 5000 RPM) and final emulsions may be made by microfluidization (~10,000 psi, 5 passes, Microfluidizer 110S).

Following preparation, microparticles can be stored as is or freeze-dried for future use. In order to adsorb macromolecules to the microparticles, the microparticle preparation is simply mixed with the macromolecule of interest and the resulting formulation can again be lyophilized prior to use. Generally, macromolecules are added to the microparticles to yield microparticles with adsorbed macromolecules having a weight to weight ratio of from about 0.0001:1 to 0.25:1 macromolecules to microparticles, preferably, 0.001:1 to 0.1, more preferably 0.01 to 0.05. Macromolecule content of the microparticles can be determined using standard techniques.

The microparticles of the present invention may have macromolecules entrapped or encapsulated within them, as well as having macromolecules adsorbed thereon. Thus, for example, one of skill in the art may prepare in accordance with the invention microparticles having encapsulated adjuvants with proteins adsorbed thereon, or microparticles having encapsulated proteins with adjuvants adsorbed thereon.

Once the macromolecule adsorbed microparticles are produced, they are formulated into pharmaceutical compositions or vaccines, to treat, prevent and/or diagnose a wide variety of disorders, as described above. The compositions will generally include one or more pharmaceutically acceptable excipients or vehicles such as water, saline, glycerol, polyethyleneglycol, hyaluronic acid, ethanol, etc. Additionally, auxiliary substances, such as wetting or emulsifying agents, biological buffering substances, and the like, may be present in such vehicles. A biological buffer can be virtually any solution which is pharmacologically acceptable and which provides the formulation with the desired pH, i.e., a pH in the physiological range. Examples of buffer solutions include saline, phosphate buffered saline, Tris buffered saline, Hank's buffered saline, and the like.

Adjuvants may be used to enhance the effectiveness of the pharmaceutical compositions. The adjuvants may be administered concurrently with the microparticles of the present invention, e.g., in the same composition or in separate compositions. Alternatively, an adjuvant may be administered prior or subsequent to the microparticle compositions of the present invention. In another embodiment, the adjuvant, such as an immunological adjuvant, may be encapsulated in the microparticle. Adjuvants, just as any macromolecules, may be encapsulated within the microparticles using any of the several methods known in the art. See, e.g., U.S. Pat. No. 3,523,907; Ogawa et al., *Chem Pharm. Bull*. (1988) 36:1095-1103; O'Hagan et al., *Vaccine* (1993) 11:965-969 and Jefferey et al., *Pharm. Res*. (1993) 10:362. Alternatively, adjuvants may be adsorbed on the microparticle as described above for any macromolecule. Alternatively, adjuvants may comprise the oil droplet emulsions of the present invention.

Immunological adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™) (for a further discussion of suitable submicron oil-in-water emulsions for use herein, see commonly owned, patent application Ser. No. 09/015,736, filed on Jan. 29, 1998); (3) saponin adjuvants, such as Quil A, or QS21 (e.g., Stimulon™ (Cambridge Bioscience, Worcester, Mass.)) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S 109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); (7) CpG oligonucleotides and other immunostimulating sequences (ISSs); and (8) other substances that act as immunostimulating agents to enhance the effectiveness of the composition. Alum and MF59 are preferred.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(1'-2'-dipalmitoyl-sn-glycero-3-huydroxyphosphoryloxy)-ethylamine (MTP-PE), etc.

For additional examples of adjuvants, see *Vaccine Design, The Subunit and the Adjuvant Approach*, Powell, M. F. and Newman, M. J, eds., Plenum Press, 1995)

The compositions will comprise a "therapeutically effective amount" of the macromolecule of interest. That is, an amount of macromolecule/microparticle will be included in the compositions which will cause the subject to produce a sufficient response, in order to prevent, reduce, eliminate or diagnose symptoms. The exact amount necessary will vary, depending on the subject being treated; the age and general condition of the subject to be treated; the severity of the condition being treated; in the case of an immunological response, the capacity of the subject's immune system to synthesize antibodies; the degree of protection desired and the particular antigen selected and its mode of administration, among other factors. An appropriate effective amount can be readily determined by one of skill in the art. Thus, a "therapeutically effective amount" will fall in a relatively broad range that can be determined through routine trials. For example, for purposes of the present invention, where the macromolecule is a polynucleotide, an effective dose will typically range from about 1 ng to about 1 mg, more preferably from about 10 ng to about 1 μg, and most preferably about 50 ng to about 500 ng of the macromolecule delivered per dose; where the macromolecule is an antigen, an effective dose will typically range from about 1 μg to about 100 mg, more preferably from about 10 μg to about 1 mg, and most preferably about 50 μg to about 500 μg of the macromolecule delivered per dose.

Once formulated, the compositions of the invention can be administered parenterally, e.g., by injection. The compositions can be injected either subcutaneously, intraperitoneally, intravenously or intramuscularly. Other modes of administration include nasal, oral and pulmonary administration, suppositories, and transdermal or transcutaneous applications. Dosage treatment may be a single dose schedule or a multiple dose schedule. A multiple dose schedule is one in which a primary course of administration may be with 1-10 separate doses, followed by other doses given at subsequent time intervals, chosen to maintain and/or reinforce the therapeutic response, for example at 1-4 months for a second dose, and if needed, a subsequent dose(s) after several months. The dosage regimen will also, at least in part, be determined by the need of the subject and be dependent on the judgment of the practitioner.

Furthermore, if prevention of disease is desired, the macromolecules in vaccines, are generally administered prior to primary infection with the pathogen of interest. If treatment is desired, e.g., the reduction of symptoms or recurrences, the macromolecules are generally administered subsequent to primary infection.

2. Oil Droplet Emulsions

In another embodiment of the present invention, an oil droplet emulsion is prepared comprising a metabolizable oil and an emulsifying agent. Molecules such as an oligonucleotide comprising at least one CpG motif may be combined with the oil droplet emulsion to form an adjuvant. The oil droplet emulsion preferably comprises a metabolizable oil and an emulsifying agent, wherein the oil and the emulsifying agent are present in the form of an oil-in-water emulsion having oil droplets substantially all of which are less than one micron in diameter. Such droplets show a surprising superiority over adjuvant compositions containing oil and emulsifying agents in which the oil droplets are significantly larger than those provided by the present invention. In preferred embodiments, the emulsion is positively charged as a result of a cationic detergent being used as the emulsifying agent or, alternatively, contains a cationic detergent separate from the emulsifying agent. This allows for the adsorption of nucleotide antigenic molecules, such as CpG oligonucleotides or viral DNA. Alternatively, the use of an anionic detergent allows for the adsorption of molecules such as proteins.

Although individual components of the adjuvant compositions of the present invention are known, such compositions have not been combined in the same manner. Accordingly, the individual components, although described below both generally and in some detail for preferred embodiments, are well known in the art, and the terms used herein, such as metabolizable oil, emulsifying agent, immunostimulating agent, muramyl peptide, and lipophilic muramyl peptide, are sufficiently well known to describe these compounds to one skilled in the art without further description.

One component of these compositions is a metabolizable, non-toxic oil, preferably one of about 6 to about 30 carbon atoms including, but not limited to, alkanes, alkenes, alkynes, and their corresponding acids and alcohols, the ethers and esters thereof, and mixtures thereof. The oil can be any vegetable oil, fish oil, animal oil or synthetically prepared oil which can be metabolized by the body of the host animal to which the adjuvant will be administered and which is not toxic to the subject. The host animal is typically a mammal, and preferably a human. Mineral oil and similar toxic petroleum distillate oils are expressly excluded from this invention.

The oil component of this invention can also be any long chain alkane, alkene or alkyne, or an acid or alcohol derivative thereof either as the free acid, its salt or an ester such as a mono-, or di- or triester, such as the triglycerides and esters of 1,2-propanediol or similar poly-hydroxy alcohols. Alcohols can be acylated employing amino- or poly-functional acid, for example acetic acid, propanoic acid, citric acid or the like. Ethers derived from long chain alcohols which are oils and meet the other criteria set forth herein can also be used.

The individual alkane, alkene or alkyne moiety and its acid or alcohol derivatives will generally have about 6 to about 30 carbon atoms. The moiety can have a straight or branched chain structure. It can be fully saturated or have one or more double or triple bonds. Where mono or poly ester- or ether-based oils are employed, the limitation of about 6 to about 30 carbons applies to the individual fatty acid or fatty alcohol moieties, not the total carbon count.

Any metabolizable oil, particularly from an animal, fish or vegetable source, can be used herein. It is essential that the oil be metabolized by the host to which it is administered, otherwise the oil component can cause abscesses, granulomas or even carcinomas, or (when used in veterinary practice) can make the meat of vaccinated birds and animals unacceptable for human consumption due to the deleterious effect the unmetabolized oil can have on the consumer.

Exemplary sources for vegetable oils include nuts, seeds and grains. Peanut oil, soybean oil, coconut oil, and olive oil, the most commonly available, exemplify the nut oils. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like can also be used.

The technology for obtaining vegetable oils is well developed and well known. The compositions of these and other similar oils can be found in, for example, the Merck Index, and source materials on foods, nutrition and food technology.

The 6-10 carbon fatty acid esters of glycerol and 1,2-propanediol, while not occurring naturally in seed oils, can be prepared by hydrolysis, separation and esterification of the appropriate materials starting from the nut and seed oils. These products are commercially available under the name NEOBEE® from PVO International, Inc., Chemical Specialties Division, 416 Division Street, Boongon, N.J., and others.

Oils from any animal source can also be employed in the adjuvants and immunogenic compositions of this invention Animal oils and fats are usually solids at physiological temperatures due to the fact that they exist as triglycerides and have a higher degree of saturation than oils from fish or vegetables. However, fatty acids are obtainable from animal fats by partial or complete triglyceride saponification which provides the free fatty acids. Fats and oils from mammalian milk are metabolizable and can therefore be used in the practice of this invention. The procedures for separation, purification, saponification and other means necessary for obtaining pure oils from animal sources are well known in the art.

Most fish contain metabolizable oils which can be readily recovered. For example, cod liver oil, shark liver oils, and whale oil such as spermaceti exemplify several of the fish oils which can be used herein. A number of branched chain oils are synthesized biochemically in 5-carbon isoprene units and are generally referred to as terpenoids. Shark liver oil contains a branched, unsaturated terpenoid known as squalene, 2,6,10,15,19,23-hexamethyl-2,6,10,14,18,22-tetracosahexaene which is particularly preferred herein. Squalane, the saturated analog to squalene, is also a particularly preferred oil. Fish oils, including squalene and squalane, are readily available from commercial sources or can be obtained by methods known in the art.

The oil component of these adjuvants and immunogenic compositions will be present in an amount from about 0.5% to about 20% by volume but preferably no more than about 15%, especially in an amount of about 1% to about 12%. It is most preferred to use from about 1% to about 4% oil.

The aqueous portion of these adjuvant compositions is preferably buffered saline or, more preferably, unadulterated water. Because these compositions are intended for parenteral administration, it is preferable to make up final buffered solutions used as immunogenic compositions so that the tonicity, i.e., osmolality, is essentially the same as normal physiological fluids in order to prevent post-administration swelling or rapid absorption of the composition because of differential ion concentrations between the composition and physiological fluids. It is also preferable to buffer the saline in order to maintain pH compatible with normal physiological conditions. Also, in certain instances, it can be necessary to maintain the pH at a particular level in order to ensure the stability of certain composition components such as the glycopeptides.

Any physiologically acceptable buffer can be used herein, but phosphate buffers are preferred. Other acceptable buffers such acetate, tris, bicarbonate, carbonate, or the like can be used as substitutes for phosphate buffers. The pH of the aqueous component will preferably be between about 6.0-8.0.

When the microemulsion is initially prepared, however, unadulterated water is preferred as the aqueous component of the emulsion. Increasing the salt concentration makes it more difficult to achieve the desired small droplet size. When the final immunogenic compositions is prepared from the adjuvant, the antigenic material can be added in a buffer at an appropriate osmolality to provide the desired immunogenic composition.

The quantity of the aqueous component employed in these compositions will be that amount necessary to bring the value of the composition to unity. That is, a quantity of aqueous component sufficient to make 100% will be mixed, with the other components listed above, in order to bring the compositions to volume.

A substantial number of emulsifying and suspending agents are generally used in the pharmaceutical sciences. These include naturally derived materials such as gums from trees, vegetable protein, sugar-based polymers such as alginates and cellulose, and the like. Certain oxypolymers or polymers having a hydroxide or other hydrophilic substituent on the carbon backbone have surfactant activity, for example, povidone, polyvinyl alcohol, and glycol ether-based mono- and poly-functional compounds. Long chain fatty-acid-derived compounds form a third substantial group of emulsifying and suspending agents which could be used in this invention. Any of the foregoing surfactants are useful so long as they are non-toxic.

Specific examples of suitable emulsifying agents (also referred to as surfactants or detergents) which can be used in accordance with the present invention include the following:

1. Water-soluble soaps, such as the sodium, potassium, ammonium and alkanol-animonium salts of higher fatty acids ($C_{10}$-$C_{22}$), and, particularly sodium and potassium tallow and coconut soaps.

2. Anionic synthetic non-soap detergents, which can be represented by the water-soluble salts of organic sulfuric acid reaction products having in their molecular structure an alkyl radical containing from about 8 to about 22 carbon atoms and a radical selected from the group consisting of sulfonic acid and sulfuric acid ester radicals. Examples of these are the sodium or potassium alkyl sulfates, derived from tallow or coconut oil; sodium or potassium alkyl benzene sulfonates; sodium alkyl glyceryl ether sulfonates; sodium coconut oil fatty acid monoglyceride sulfonates and sulfates; sodium or potassium salts of sulfuric acid asters of the reaction product of one mole of a higher fatty alcohol and about 1 to about 6 moles of ethylene oxide; sodium or potassium alkyl phenol ethylene oxide ether sulfonates, with 1 to about 10 units of ethylene oxide per molecule and in which the alkyl radicals contain from about 8 to about 12 carbon atoms; the reaction product of fatty acids esterified with isethionic acid and neutralized with sodium hydroxide; sodium or potassium salts of fatty acid amide of a methyl tauride; and sodium and potassium salts of $SO_3$— sulfonated $C_{10}$-$C_{24}$ α-olefins.

3. Nonionic synthetic detergents made by the condensation of alkylene oxide groups with an organic hydrophobic compound. Typical hydrophobic groups include condensation products of propylene oxide with propylene glycol, alkyl phenols, condensation product of propylene oxide and ethylene diamine, aliphatic alcohols having about 8 to about 22 carbon atoms, and amides of fatty acids.

4. Nonionic detergents, such as amine oxides, phosphine oxides and sulfoxides, having semipolar characteristics. Specific examples of long chain tertiary amine oxides include dimethyldodecylamine oxide and bis-(2-hydroxyethyl)dodecylamine. Specific examples of phosphine oxides are found in U.S. Pat. No. 3,304,263 which issued Feb. 14, 1967, and include dimethyldodecylphosphine oxide and dimethyl-(2-hydroxydodecyl)phosphine oxide.

5. Long chain sulfoxides, including those corresponding to the formula $R^1$—SO—$R^2$ wherein $R^1$ and $R^2$ are substituted or unsubstituted alkyl radicals, the former containing from about 10 to about 28 carbon atoms, whereas $R^2$ contains from 1 to about 3 carbon atoms. Specific examples of these sulfoxides include dodecylmethyl sulfoxide and 3-hydroxy tridecyl methyl sulfoxide.

6. Ampholytic synthetic detergents, such as sodium 3-dodecylamino-propionate and sodium 3-dodecylamino-propane sulfonate.

7. Zwitterionic synthetic detergents, such as 3-(N,N-dimethyl-N-hexadecylammonio) propane-1-sulfonate and 3-(N, N-dimethyl-N-hexadecylammonio)-2hydroxy propane-1-sulfonate.

Additionally, all of the following types of emulsifying agents can be used in a composition of the present invention: (a) soaps (i.e., alkali salts) of fatty acids, rosin acids, and tall oil; (b) alkyl arene sulfonates; (c) alkyl sulfates, including surfactants with both branched-chain and straight chain hydrophobic groups, as wall as primary and secondary sulfate groups; (d) sulfates and sulfonates containing an intermediate linkage between the hydrophobic and hydrophilic groups, such as the fatty acylated methyl taurides and the sulfated fatty monoglycerides; (e) long-chain acid esters of polyethylene glycol, especially the tall oil esters; (f) polyethylene glycol ethers of alkylphenols; (g) polyethylene glycol ethers of long-chain alcohols and mercaptans; and (h) fatty acyl diethanol amides. Since surfactants can be classified in more than one manner, a number of classes of surfactants set forth in this paragraph overlap with previously described surfactant classes.

There are a number oil emulsifying agents specifically designed for and commonly used in biological situations. For example, a number of biological detergents (surfactants) are listed as such by Sigma Chemical Company on page 310-316 of its 1987 Catalog of Biochemical and Organic Compounds. Such surfactants are divided into four basic types: anionic, cationic, zwitterionic, and nonionic. Examples of anionic detergents include, but are not limited to, alginic acid, caprylic acid, cholic acid, 1-decanesulfonic acid, deoxycholic acid, 1-dodecanesulfonic acid, N-lauroylsarcosine, and taurocholic acid, and the like. Cationic detergents include, but are not limited to, cetrimide (hexadecyltrimethylammonium bromide—CTAB), benzalkonium chloride, dimethyl dioctodecyl ammonium (DDA) bromide, DOTAP, dodecyltrimethylammonium bromide, benzyldimethylhexadecyl ammonium chloride, cetylpyridinium chloride, methylbenzethonium chloride, and 4-picoline dodecyl sulfate, and the like. Examples of zwitterionic detergents include, but are not limited to, 3-[(3-cholamidopropyl)-dimethylammonio]-1-propanesulfonate (commonly abbreviated CHAPS), 3-[(cholamidopropyl)-dimethylammonio]-2-hydroxy-1-propanesulfonate (generally abbreviated CHAPSO) N-dodecyl-N,N-dimethyl-3-ammonio-1-propanesulfonate, and lyso-α-phosphatidylcholine, and the like. Examples of nonionic detergents include, but are not limited to, decanoyl-N-methylglucamide, diethylene glycol monopentyl ether, n-dodecyl β-D-glucopyranoside, ethylene oxide condensates of fatty alcohols (e.g., sold under the trade name Lubrol), polyoxyethylene ethers of fatty acids (particularly $C_{12}$-$C_{20}$ fatty acids), polyoxyethylene sorbitan fatty acid ethers (e.g., sold under the trade name Tween), and sorbitan fatty acid ethers (e.g., sold under the trade name Span), and the like. The optional component of the adjuvant compositions which results in a positively charged emulsion can be, for example, any of the cationic detergents described above. Alternatively, the cationic detergents described above can be used along with any of the oil droplet emulsions described above in order to render the emulsion positively charged.

A particularly useful group of surfactants are the sorbitan-based non-ionic surfactants. These surfactants are prepared by dehydration of sorbitol to give 1,4-sorbitan which is then reacted with one or more equivalents of a fatty acid. The fatty-acid substituted moiety can be further reacted with ethylene oxide to give a second group of surfactants.

The fatty-acid-substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1 1,g-sorbitan sesquiester or 1,4-sorbitan triester. The common names for these surfactants include, for example, sorbitan monolaurate, sorbitan monopalmitate, sorbitan monoestearate, sorbitan monooleate, sorbitan sesquioleate, and sorbitan trioleate. These surfactants are commercially available under the name SPAN® or ARLACEL®, usually with a letter or number designation which distinguishes between the various mono-, di- and triester substituted sorbitans.

SPAN® and ARLACEL® surfactants are hydrophilic and are generally soluble or dispersible in oil. They are also soluble in most organic solvents. In water they are generally insoluble but dispersible. Generally these surfactants will have a hydrophilic-lipophilic balance (HLB) number between 1.8 to 8.6. Such surfactants can be readily made by means known in the art or are commercially available from, for example, ICI America's Inc., Wilmington, Del. under the registered mark ATLAS®.

A related group of surfactants comprises polyoxyethylene sorbitan monoesters and polyoxyethylene sorbitan triesters. These materials are prepared by addition of ethylene oxide to a 1,4-sorbitan monoester or triester. The addition of polyoxyethylene converts the lipophilic sorbitan mono- or triester surfactant to a hydrophilic surfactant generally soluble oil dispersible in water and soluble to varying degrees in organic liquids.

These materials, commercially available under the mark TWEEN® are useful for preparing oil-in-water emulsions and dispersions or for the solubilization of oils and making anhydrous ointments water-soluble or washable. The TWEEN® surfactants can be combined with a related sorbitan monoester or triester surfactants to promote emulsion stability. TWEEN® surfactants generally have a HLB value falling between 9.6 to 16.7.

A third group of non ionic surfactants which could be used alone or in combination with SPAN®, ARLACEL®, and TWEEN® surfactants are the polyoxyethylene fatty acids made by the reaction of ethylene oxide with a long-chain fatty acid. The most commonly available surfactant of this type is solid under the name MYRJ® and is a polyoxyethylene derivative of stearic acid. MYRJ® surfactants are hydrophilic and soluble or dispersible in water like TWEEN® surfactants. The MYRJ® surfactants can be blended with TWEEN® surfactants, or with TWEEN®/SPAN® or ARLACEL® surfactant mixtures for use in forming emulsions. MYRJ® surfactants can be made by methods known in the art or are available commercially from ICI America's Inc.

A fourth group of polyoxyethylene based nonionic surfactants are the polyoxyethylene fatty acid ethers derived from lauryl, acetyl, stearyl and oleyl alcohols. These materials are prepared as above by addition of ethylene oxide to a fatty alcohol. The commercial name for these surfactants is BRIJ°. BRIJ° surfactants can be hydrophilic or lipophilic depending on the size of the polyoxyethylene moiety in the surfactant. While the preparation of these compounds is available from the art, they are also readily available from such commercial sources as ICI America's Inc.

Other non-ionic surfactants which could potentially be used in the practice of this invention are for example: polyoxyethylene, polyol fatty acid esters, polyoxyethylene ether, polyoxypropylene fatty ethers, bee's wax derivatives containing polyoxyethylene, polyoxyethylene lanolin derivative, polyoxyethylen fatty glyceride, glycerol fatty acid esters or other polyoxyethylene acid alcohol or ether derivatives of long-chain fatty acids of 12-22 carbon atoms.

As the adjuvant and the immunogenic compositions of this invention are intended to be multi-phase systems, it is preferable to choose an emulsion-forming non-ionic surfactant which has an HLB value in the range of about 7 to about 16. This value can be obtained through the use of a single non-ionic surfactant such as a TWEEN® surfactant or can be achieved by the use of a blend of surfactants such as with a sorbitan mono, di- or triester based surfactant; a sorbitan ester polyoxyethylene fatty acid; a sorbitan ester in combination with a polyoxyethylene lanolin derived surfactant; a sorbitan ester surfactant in combination with a high HLB polyoxyethylene fatty ether surfactant; or a polyethylene fatty ether surfactant or polyoxyethylene sorbitan fatty acid.

It is more preferred to use a single nonionic surfactant, most particularly a TWEEN® surfactant, as the emulsion stabilizing non-ionic surfactant in the practice of this invention. The surfactant named TWEEN® 80, otherwise known as polysorbate 80 for polyoxyethlyene 20 sorbitan monooleate, is the most preferred of the foregoing surfactants.

Sufficient droplet size reduction can usually be effected by having the surfactant present in an amount of 0.02% to 2.5% by weight (w/w). An amount of 0.05% to 1% is preferred with 0.01 to 0.5% being especially preferred.

The manner in which the droplet size of the invention is reached is not important to the practice of the present invention. One manner in which submicron oil droplets can be obtained is by use of a commercial emulsifiers, such as model number 110Y available from Microfluidics, Newton, Mass. Examples of other commercial emulsifiers include Gaulin Model 30CD (Gaulin, Inc., Everett, Mass.) and Rainnie Minilab Type 8.30H (Miro Atomizer Food and Dairy, Inc., Hudson, Wis.). These emulsifiers operated by the principle of high shear forces developed by forcing fluids through small apertures under high pressure. When the model 110Y is operated at 5,000-30,000 psi, oil droplets having diameters of 100-750 nm are provided.

The size of the oil droplets can be varied by changing the ratio of detergent to oil (increasing the ratio decreases droplet size, operating pressure (increasing operating pressure reduces droplet size), temperature (increasing temperature decreases droplet size), and adding an amphipathic immunostimulating agent (adding such agents decreases droplet size). Actual droplet size will vary with the particular detergent, oil, and immunostimulating agent (if any) and with the particular operating conditions selected. Droplet size can be verified by use of sizing instruments, such as the commercial Sub-Micron Particle Analyzer (Model N4MD) manufactured by the Coulter Corporation, and the parameters can be varied using the guidelines set forth above until substantially all droplets are less than 1 micron in diameter, preferably less than 0.8 microns in diameter, and most preferably less than 0.5 microns in diameter. By substantially all is meant at least about 80% (by number), preferably at least about 90%, more preferably at least about 95%, and most preferably at least about 98%. The particle size distribution is typically Gaussian, so that the average diameter is smaller than the stated limits.

The present invention may preferably be practiced by preparing an oil emulsion in the absence of other components previously taught in the prior art to be used with submicron emulsions for satisfactory immunogenicity, namely polyoxylropylene-polyoxyethlyne block polymers such as those described for use with adjuvants in U.S. Pat. Nos. 4,772,466 and 4,770,874 and in European Patent Application 0 315 153 A2.

A microemulsion composition of the invention may comprise a metabolizable oil in water and an emulsifying agent other than a POP-POE copolymer. The emulsifying agent need not have any specific immunostimulating activity, since the oil composition by itself can function as an adjuvant when the oil droplets are in the sub-micron range. However, increased immunostimulating activity can be provided by including any of the known immunostimulating agents in the composition. These immunostimulating agents can either be separate from the emulsifying agent and the oil or the immunostimulating agent and the emulsifying agent can be one and the same molecule. Examples of the former situation include metabolizable oils mixed with killed mycobacteria, such as *Mycobacterium tuberculosis*, and subcellular components thereof. Additional immunostimulating substances include the muramyl peptides that are components of the cell walls of such bacteria, and include derivatives thereof. Examples of the joint emulsifying agent/immunostimulating agent are the lipophilic muramyl peptides described in Sanchez-Pescador et al., *J. Immunol.*, 1988, 141, 1720-1727, the disclosure of which is incorporated herein by reference in its entirety. These materials comprise the basic N-acetylmuramyl peptide (a hydrophilic moiety) that acts is an immunostimulating group, but also include a lipophilic moiety that provides surface-active characteristics to the resulting compound. Such compounds, as well as other types of amphipathic immunostimulating substances, act as both immunostimulating agents and emulsifying agents and are preferred in the practice of the present invention. In addition, it is also possible to practice the present invention by using a amphipathic immunostimulating substance in combination with a second immunostimulating substance that is not amphipathic. An example would be use of a lipophilic muramyl peptide in combination with an essentially unsubstituted (i.e., essentially hydrophilic) muramyl dipeptide.

A preferred oil droplet emulsion is MF59. MF59 can be made according to the procedures described in, for example, Ott et al., *Vaccine Design: The Subunit And Adjuvant Approach*, 1995, M. F. Powell and M. J. Newman, Eds., Plenum Press, New York, p. 277-296; Singh et al., *Vaccine*, 1998, 16, 1822-1827; Ott et al., *Vaccine*, 1995, 13, 1557-1562; and Valensi et al., *J. Immunol.*, 1994, 153, 4029-39, the disclosures of which are incorporated herein by reference in their entirety.

Other oil droplet emulsions include, for example, SAF, containing 10% Squalane, 0.4% Tween 80, 5% pluronic-blocked polymer L121, and thr-MDP either microfluidized into a submicron emulsion or vortexed to generate a larger particle size emulsion, and Ribi® adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (DetoxJ) (for a further discussion of suitable submicron oil-in-water emulsions for use herein, see commonly owned, patent application Ser. No. 09/015,736, filed on Jan. 29, 1998).

After preparing the microemulsion of the invention, macromolecules may be adsorbed thereto to increase the adjuvant effect of the microemulsion. The additional component of the compositions of the present invention preferably is an oligonucleotide which comprises at least one CpG motif. As used herein, the phrase "CpG motif" refers to a dinucleotide portion of an oligonucleotide which comprises a cytosine nucleotide followed by a guanosine nucleotide. Such oligonucleotides can be prepared using conventional oligonucleotide synthesis well known to the skilled artisan. Preferably, the oligonucleotides of the invention comprise a modified backbone, such as a phosphorothioate or peptide nucleic acid, so as to confer nuclease resistance to the oligonucleotide. Modified backbones are well known to those skilled in the art. Preferred peptide nucleic acids are described in detail in U.S. Pat. Nos. 5,821,060, 5,789,573, 5,736,392, and 5,721,102, Japanese Patent No. 10231290, European Patent No. 839, 828, and PCT Publication Numbers WO 98/42735, WO 98/42876, WO 98/36098, WO 98/27105, WO 98/20162, WO 98/16550, WO 98/15648, WO 98/04571, WO 97/41150, WO 97/39024, and WO 97/38013, the disclosures of which are incorporated herein by reference in their entirety.

The oligonucleotide preferably comprises between about 6 and about 100 nucleotides, more preferably between about 8 and about 50 nucleotides, most preferably between about 10 and about 40 nucleotides. In addition, the oligonucleotides of the invention can comprise substitutions of the sugar moieties and nitrogenous base moieties. Preferred oligonucleotides are disclosed in, for example, Krieg et al., *Proc. Natl. Acad. Sci. USA*, 1998, 95, 12631-12636, Klinman et al., *Proc. Natl. Acad. Sci. USA*, 1996, 93, 2879-2883, Weiner et al., *Proc. Natl. Acad. Sci. USA*, 1997, 94, 10833-10837, Chu et al., *J. Exp. Med.*, 1997, 186, 1623-1631, Brazolot-Millan et al., *Proc. Natl. Acad. Sci. USA*, 1998, 95, 15553-15558, Ballas et al., *J. Immunol.*, 1996, 157, 1840-1845, Cowdery et al., *J. Immunol.*, 1996, 156, 4570-4575, Halpern et al., *Cell. Immunol.*, 1996, 167, 72-78, Yamamoto et al., *Jpn. J. Cancer Res.*, 1988, 79, 866-873, Stacey et al., *J. Immunol.*, 1996, 157, 2116-2122, Messina et al., *J. Immunol.*, 1991, 147, 1759-1764, Yi et al., *J. Immunol.*, 1996, 157, 4918-4925, Yi et al., *J. Immunol.*, 1996, 157, 5394-5402, Yi et al., *J. Immunol.*, 1998, 160, 4755-4761, Roman et al., *Nat. Med.*, 1997, 3, 849-854, Davis et al., *J. Immunol.*, 1998, 160, 870-876, Lipford et al., *Eur. J. Immunol.*, 1997, 27, 2340-2344, Moldoveanu et al., *Vaccine*, 1988, 16, 1216-1224, Yi et al., *J. Immunol.*, 1998, 160, 5898-5906, PCT Publication WO 96/02555, PCT Publication WO 98/16247, PCT Publication WO 98/18810, PCT Publication WO 98/40100, PCT Publication WO 98/55495, PCT Publication WO 98/37919, and PCT Publication WO 98/52581, the disclosures of which are incorporated herein by reference in their entirety. It is to be understood that the oligonucleotides of the invention comprise at least one CpG motif but can contain a plurality of CpG motifs.

Preferred oligonucleotides comprise nucleotide sequences such as, for example, tccatgacgttcctgatgct (SEQ ID NO:1), ataatcgacgttcaagcaag (SEQ ID NO:2), ggggtcaacgtgaggggg (SEQ ID NO:3), tctcccagcgtgcgccat (SEQ ID NO:4), gagaacgctcgaccttcgat (SEQ ID NO:5), tccatgtcgttcctgatgct (SEQ ID NO:6), tccatgacgttcctgatgct (SEQ ID NO:7), gctagacgttagcgt (SEQ ID NO:8), atcgactctcgagcgttctc (SEQ ID NO:9), gaaccttccatgctgttccg (SEQ ID NO:10), gctagatgtagcgt (SEQ ID NO:11), tcaacgtt (SEQ ID NO:12), gcaacgtt (SEQ ID NO:13), tcgacgtc (SEQ ID NO:14), tcagcgct (SEQ ID NO:15), tcaacgct (SEQ ID NO:16), tcatcgat (SEQ ID NO:17), tcttcgaa (SEQ ID NO:18), tgactgtgaacgttcgagatga (SEQ ID NO:19), tgactgtgaacgttagcgatga (SEQ ID NO:20), tgactgtgaacgttagagcgga (SEQ ID NO:21), gttttgcgcaacgttgt- tgccat (SEQ ID NO:22), atggcaacaacgttgcgcaaac (SEQ ID NO:23), cattggaaaacgttcttcgggg (SEQ ID NO:24), ccccgaagaacgttttccaatg (SEQ ID NO:25), attgacgtcaat (SEQ ID NO:26), ctttccattgacgtcaatgggt (SEQ ID NO:27), and tccatacgttcctgacgtt (SEQ ID NO:28). In preferred embodiments of the invention, the oligonucleotide comprises a CpG motif flanked by two purines at the 5' side of the motif and two pyrimidines at the 3' side of the motif. It is to be understood, however, that any oligonucleotide comprising a CpG motif can be used in the present invention as long as the oligonucleotide induces an increase in Th1 lymphocyte stimulation when combined with the oil droplet emulsions described herein.

In another preferred embodiment, the macromolecule is immunogenic DNA or immunogenic protein adsorbed to the microemulsion. Such adsorption creates a microemulsion with a strong adjuvant effect.

The present invention is also directed to immunogenic compositions comprising the microemulsions described above with adsorbed antigenic and/or immunogenic molecules. The adjuvant compositions are generally prepared from the ingredients described above prior to combining the adjuvant with the antigenic substance that will be used in the immunogenic composition. The word antigen or antigenic substance refers to any substance, including a protein or protein-polysaccharide, protein-lipopolysaccharide, polysaccharide, lipopolysaccharide, viral subunit, whole virus or whole bacteria which, when foreign to the blood stream of an animal, on gaining access to the tissue of such an animal, stimulates the formation of specific antibodies and reacts specifically in vivo or in vitro with a homologous antibody. Moreover, it stimulates the proliferation of T-lymphocytes, preferably Th1 lymphocytes, with receptors for the antigen and can react with the lymphocytes to initiate the series of responses designated cell-mediated immunity.

A hapten is within the scope of this definition of antigen. A hapten is that portion of an antigenic molecule or antigenic complex that determines it immunological specificity. Commonly, a hapten is a peptide or polysaccharide in naturally occurring antigens. In artificial antigens it can be a low molecular weight substance such as an arsanilic acid derivative. A hapten will react specifically in vivo or in vitro with homologous antibodies or T lymphocytes. Alternative descriptors are antigenic determinant, antigenic structural grouping and haptenic grouping.

In preferred embodiments of the invention, the antigenic substance is derived from a virus such as, for example, human immunodeficiency virus (HIV), hepatitis B virus (HBV), hepatitis C virus (HCV), herpes simplex virus (HSV), cytomegalovirus (CMV), influenza virus (flu), and rabies virus. Preferably, the antigenic substance is selected from the group consisting of HSV glycoprotein gD, HIV glycoprotein gp120, and HIV p55 gag. In other preferred embodiments of the invention, the antigenic substance is derived from a bacterium such as, for example, *Helicobacter pylori, Haemophilus influenza*, cholera, diphtheria, tetanus, *Neisseria meningitidis*, and pertussis. In other preferred embodiments of the invention, the antigenic substance is from a parasite such as, for example, a malaria parasite. In another preferred embodiment of the present invention, the antigen is adsorbed to the surface of a microparticle of the present invention.

Antigens can be produced by methods known in the art or can be purchased from commercial sources. Antigens within the scope of this invention include whole inactivated virus particles, isolated virus proteins and protein subunits, whole cells and bacteria, cell membrane and cell wall proteins, and the like. Some preferred antigens are described below.

Herpes simplex virus (HSV) rgD2 is a recombinant protein produced in genetically engineered Chinese hamster ovary cells. This protein has the normal anchor region truncated, resulting in a glycosylated protein secreted into tissue culture medium. The gD2 can be purified in the CHO medium to greater than 90% purity. Human immunodeficiency virus (HIV) env-2-3 is a recombinant form of the HIV enveloped protein produced in genetically engineered *Saccharomyces cerevisae*. This protein represents the entire protein region of HIV gp120 but is nonglycosylated and denatured as purified from the yeast. HIV gp120 is a fully glycosylated, secreted form of gp120 produced in CHO cells in a fashion similar to the gD2 above. Additional HSV antigens suitable for use in immunogenic compositions are described in PCT Publications WO 85/04587 and WO 88/02634, the disclosures of which are incorporated herein by reference in their entirety. Mixtures of gB and gD antigens, which are truncated surface antigens lacking the anchor regions, are particularly preferred.

Influenza antigens suitable for use in immunogenic compositions are commercially available. Antigens that can be used in the following examples include, but are not limited to FLUOGEN® (manufactured by Parke-Davis), Duphar (manufactured by Duphar B. V.), and influenza vaccine batch A41 (manufactured by Instituto Vaccinogeno Pozzi).

Malaria antigens suitable for use in immunogenic compositions are described in U.S. patent application Serial No. 336,288, filed Apr. 11, 1989, and in U.S. Pat. No. 4,826,957, the disclosures of which are incorporated herein by reference in their entirety.

Additional HIV antigens suitable for use in immunogenic compositions are described in U.S. application serial No. 490,858, filed Mar. 9, 1990, and published European application number 181150 (May 14, 1986), disclosures of which are incorporated herein by reference in their entirety.

Cytomegalovirus antigens suitable for use in immunogenic compositions are described in U.S. Pat. No. 4,689,225, U.S. application serial number 367,363, filed Jun. 16, 1989 and PCT Publication WO 89/07143, the disclosures of which are incorporated herein by reference in their entirety.

Hepatitis C antigens suitable for use in immunogenic compositions are described in PCT/US88/04125, published European application number 318216 (May 31, 1989), published Japanese application number 1-500565 filed Nov. 18, 1988, Canadian application 583,561, and EPO 388,232, disclosures of which are incorporated herein by reference in their entirety. A different set of HCV antigens is described in European patent application 90/302866.0, filed Mar. 16, 1990, and U.S. application serial number 456,637, filed Dec. 21, 1989, and PCT/US90/01348, the disclosures of which are incorporated herein by reference in their entirety.

Immunogenic compositions of the invention can be used to immunize birds and mammals against diseases and infection, including without limitation cholera, diphtheria, tetanus, pertussis, influenza, measles, meningitis, mumps, plague, poliomyelitis, rabies, Rocky Mountain spotted fever, rubella, smallpox, typhoid, typhus, feline leukemia virus, and yellow fever.

The compositions of an immunogenic composition of the invention will employ an effective amount of an antigen. That is, there will be included an amount of antigen which, in combination with the adjuvant, will cause the subject to produce a specific and sufficient immunological response, preferably a Th1 lymphocyte response, so as to impart protection to the subject from the subsequent exposure to virus, bacterium, fungus, mycoplasma, or parasite immunized against.

No single dose designation can be assigned which will provide specific guidance for each and every antigen which can be employed in this invention. The effective amount of antigen will be a function of its inherent activity and purity and is empirically determined by those of ordinary skill in the art via routine experimentation. It is contemplated that the adjuvant compositions of this invention can be used in conjunction with whole cell or viral immunogenic compositions as well as with purified antigens or protein subunit or peptide immunogenic compositions prepared by recombinant DNA techniques or synthesis. Since the adjuvant compositions of the invention are stable, the antigen and emulsion can mixed by simple shaking. Other techniques, such as passing a mixture of the adjuvant and solution or suspension of the antigen rapidly through a small opening (such as a hypodermic needle) readily provides a useful immunogenic composition.

The immunogenic compositions according to the present invention comprise about 1 nanogram to about 1000 micrograms of nucleic acid, preferably DNA such as, for example, CpG oligonucleotides. In some preferred embodiments, the immunogenic compositions contain about 10 nanograms to about 800 micrograms of nucleic acid. In some preferred embodiments, the immunogenic compositions contain about 0.1 to about 500 micrograms of nucleic acid. In some preferred embodiments, the immunogenic compositions contain about 1 to about 350 micrograms of nucleic acid. In some preferred embodiments, the immunogenic compositions contain about 25 to about 250 micrograms of nucleic acid. In some preferred embodiments, the immunogenic compositions contain about 100 micrograms nucleic acid. One skilled in the art can readily formulate an immunogenic composition comprising any desired amount of nucleic acid. The immunogenic compositions according to the present invention are provided sterile and pyrogen free. The immunogenic compositions can be conveniently administered in unit dosage form and can be prepared by any of the methods well known in the pharmaceutical art, for example, as described in *Remington's Pharmaceutical Sciences* (Mack Pub. Co., Easton, Pa., 1980), the disclosure of which is incorporated herein by reference in its entirety.

The present invention is also directed to methods of stimulating an immune response in a host animal comprising administering to the animal an immunogenic composition described above in an amount effective to induce an immune response. The host animal is preferably a mammal, more preferably a human. Preferred routes of administration include, but are not limited to, intramuscular, intraperitoneal, intradermal, subcutaneous, intravenous, intraarterially, intraoccularly and oral as well as transdermally or by inhalation or suppository. Most preferred routes of administration include intramuscular, intraperitoneal, intradermal and subcutaneous injection. According to some embodiments of the present invention, the immunogenic composition is administered to a host animal using a needleless injection device, which are well known and widely available. One having ordinary skill in the art can, following the teachings herein, use needleless injection devices to deliver immunogenic compositions to cells of an individual.

The present invention is also directed to methods of immunizing a host animal against a viral, bacterial, or parasitic infection comprising administering to the animal an immunogenic composition described above in an amount effective to induce a protective response. The host animal is preferably a mammal, more preferably a human. Preferred routes of administration are described above. While prophylactic or therapeutic treatment of the host animal can be directed to any pathogen, preferred pathogens, including, but not limited to, the viral, bacterial and parasitic pathogens described above.

The present invention is also directed to methods of increasing a Th1 immune response in a host animal comprising administering to the animal an immunogenic composition described above in an amount effective to induce a Th1 immune response. The host animal is preferably a mammal, more preferably a human. Preferred routes of administration are described above. One skilled in the art is readily familiar with Th1 lymphocytes and responses and measurements thereof.

The present invention contemplates the use of microparticles or microemulsions with adsorbed antigens used to elicit an immune response alone, or in combination with each other. That is, the invention encompasses microparticles with adsorbed antigen, microemulsions with adsorbed antigen or immunostimulating molecule, and the combination of microparticles with adsorbed antigen together with microemulsions with adsorbed antigen or immunostimulating molecule.

As demonstrated by the following Examples, the present invention's microparticles with adsorbed macromolecules elicit strong immune responses. Additionally, the present invention's oil droplet emulsions also elicit strong immune responses. The combination of the present invention's microparticles with adsorbed macromolecules and the present invention's oil droplet emulsion adjuvants is therefore a powerful tool for eliciting immune responses. The invention is further illustrated by way of the following Examples which are intended to elucidate the invention. The foregoing examples are meant to illustrate the invention and are not to be construed to limit the invention in any way. Those skilled in the art will recognize modifications that are within the spirit and scope of the invention. All references cited herein are hereby incorporated by reference in their entirety.

C. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Preparation of Blank Microparticles Using PVA as an Emulsion Stabilizer

Blank microparticles (e.g., without adsorbed or entrapped macromolecules) were made using polyvinyl alcohol (PVA) as follows. Solutions used:

(1) 6% RG 504 PLG (Boehringer Ingelheim) in dichloromethane.

(2) 10% polyvinyl alcohol (PVA) (ICN) in water.

In particular, the microparticles were made by combining 10 ml of polymer solution with 1.0 ml of distilled water and homogenizing for 3 minutes using an Omni benchtop homogenizer with a 10 mm probe at 10K rpm to form a water/oil (w/o) emulsion. The w/o emulsion was added to 40 ml of the 10% PVA solution, and homogenized for 3 minutes, to form a water/oil/water (w/o/w) emulsion. The w/o/w emulsion was left stirring overnight for solvent evaporation, forming microparticles. The formed microparticles were washed with water by centrifugation 4 times, and lyophilized. The microparticles were then sized in a Malvern Master sizer for future use.

Example 2

Preparation of Blank Microparticles Using CTAB

Blank microparticles were produced using CTAB as follows. Solutions used:

(1) 4% RG 504 PLG (Boehringer Ingelheim) in dimethyl chloride.

(2) 0.5% CTAB (Sigma Chemical Co., St. Louis, Mo.) in water.

In particular, the microparticles were made by combining 12.5 ml of polymer solution with 1.25 ml of distilled water and homogenizing for 3 minutes using an Omni benchtop homogenizer with a 10 mm probe at 10K rpm to form a w/o emulsion. The w/o emulsion was added to 50 ml of the 0.5% CTAB solution and homogenized for 3 minutes to form a w/o/w emulsion. The w/o/w emulsion was left stirring overnight for solvent evaporation, forming microparticles. The formed microparticles were then filtered through a 38μ mesh, washed with water by centrifugation 4 times, and lyophilized. The microparticles were then sized in a Malvern Master sizer for future use.

Example 3

Preparation of Blank Microparticles Using SDS

Blank microparticles were produced using SDS as follows. Solutions used:

(1) 6% RG 504 PLG (Boehringer Ingelheim) in dimethyl chloride.

(2) 1% SDS (Sigma Chemical Co., St. Louis, Mo.) in water.

In particular, the microparticles were made by combining 12.5 ml of polymer solution with 50 ml of the SDS solution and homogenizing for 3 minutes using an Omni benchtop homogenizer with a 10 mm probe at 10K rpm. The emulsion was left stirring overnight for solvent evaporation. The formed microparticles were filtered through a 38μ mesh, washed with water by centrifugation 4 times, and lyophilized for future use. The microparticles were then sized in a Malvern Master sizer for future use.

Example 4

Adsorption of Protein to Blank Microparticles

Protein was adsorbed to microparticles as follows.

A. 1% and 3% Theoretical Load of p55gag

In order to achieve 1% and 3% theoretical loads, 50 mg of the lyophilized blank SDS/PLG microparticles produced as in Example 3 were placed in a Nalgene centrifuge tube and 10 ml of 25 mM Borate buffer, pH 9, with 6M urea containing p55gag protein (Chiron Corporation, Berkeley, Calif.) was added: (a) for 1% theoretical load 10 ml of a 50 µg/ml p55gag solution was used; and (b) for 3% theoretical load 10 ml of a 150 µg/ml p55gag solution was used. The mixture was incubated with rocking overnight at room temperature. The next day, the microparticles were centrifuged and analyzed for protein load by base hydrolysis followed by a bicinchoninic assay (BCA; Pierce, Rockford, Ill.), to determine the amount adsorbed. The microparticles were washed twice with 10 ml Borate/6M urea buffer and twice with 30 ml water, and lyophilized for future use.

B. 1% Theoretical Load of HCV Core Antigen

In order to achieve 1% theoretical load, 50 mg of the lyophilized blank SDS/PLG microparticles were placed in a Nalgene centrifuge tube and 10 ml of 30 mM citrate buffer, pH 6.5, with 6M urea containing monomeric HCV core protein (10 ml of a 50 µg/ml HCV core protein solution; Chiron Corporation, Berkeley, Calif.) was added. The mixture was incubated with rocking overnight at room temperature. The next day, the microparticles were centrifuged and analyzed for protein load by base hydrolysis followed by a bicinchoninic assay (BCA; Pierce, Rockford, Ill.), for HCV concentration to determine the amount adsorbed. The microparticles were washed twice with 30 ml citrate/6M urea buffer and twice with 30 ml water, and lyophilized for future use.

Example 5

Adsorption Efficiency of Microparticles

The lyophilized microparticles with adsorbed protein from Example 4 were analyzed for total adsorbed protein using base hydrolysis as follows. 10 mg of the lyophilized adsorbed particles were hydrolyzed for four hours in 2 ml 0.2N NaOH with 5% SDS, neutralized, and diluted 1:10 and analyzed for protein content using the MicroBCA protein assay (Pierce, Rockford, Ill.). As shown in Table 1, microparticles with modified surfaces prepared with detergents like CTAB and SDS, both adsorbed protein more efficiently than microparticles made using solely PVA.

TABLE 1

| Microparticle Type | Protein | Targeted Load (% w/w) | Actual Load (% w/w) |
|---|---|---|---|
| PVA-PLG | p55gag | 3% | 0.38% |
| CTAB-PLG | p55gag | 3% | 1.58% |
| SDS-PLG | p55gag | 3% | 1.36% |
| PVA-PLG | p55gag | 1% | 0.18% |
| SDS-PLG | p55gag | 0.5% | 0.45% |
| SDS-PLG | p55gag | 1% | 0.72% |
| SDS-PLG | p55gag | 1% | 0.79% |
| PVA-PLG | HCV Core | 4% | 0.3% |
| SDS-PLG | HCV Core | 1% | 0.7% |

Example 6

A Immunogenicity of gag-Adsorbed Microparticles

The gag-adsorbed microparticles, produced using PVA or SDS, as described in Example 4, as well as p55gag alone, without associated microparticles (as a negative control) and vaccinia gag-pol controls (as a positive control) were administered intramuscularly to mice. The animals were boosted at 7 and 14 days. The total dose administered is indicated in Tables 2 and 3. Spleens were collected two weeks following the last immunization and CTL activity assayed as described in Doe et al., *Proc. Natl. Acad. Sci.* (1996) 93:8578-8583.

The lymphocyte cultures were prepared as follows. Spleen cells (sc) from immunized mice were cultured in 24-well dishes at $5 \times 10^6$ cells per well. Of those cells, $1 \times 10^6$ were sensitized with synthetic epitopic peptides form HIV-$1_{SF2}$ proteins at a concentration of 10 µM for 1 hour at 37EC, washed, and cocultured with the remaining $4 \times 10^6$ untreated sc in 2 ml of culture medium [50% RPMI 1640 and 50% alpha-MEM (GIBCO)] supplemented with heat-inactivated fetal calf serum, $5 \times 10^{-5}$ M 2-mercaptoethanol, antibiotics, and 5% interleukin 2 (Rat T-Stim, Collaborative Biomedical Products, Bedford, Mass.). Cells were fed with 1 ml of fresh culture medium on days 3 and 5, and cytotoxicity was assayed on day 6.

The cytotoxic cell assay was conducted as follows. SvBALB (H-2$^d$) (SvB) and MC57 (H-2$^b$) target cells used in the $^{51}$Cr release assays express class I but not class II MHC molecules. Approximately 1×10$^6$ target cells were incubated in 200 μl of medium containing 50 μCi (1 Ci=37 Gbq) of $^{51}$Cr and synthetic HIV-1 peptides (1 mM) for 60 min and washed three times. Effector (E) cells were cultured with 5×10$^3$ target (T) cells at various E/T ratios in 200 μl of culture medium in 96-well round-bottom tissue culture plates for 4 hours. The average cpm from duplicate wells was used to calculate percent specific $^{51}$Cr release.

As shown in Tables 2 and 3, the SDS-PLG/p55 microparticles had activity comparable to the vaccinia control and was more active than the PVA-PLG/p55 microparticles and the p55gag protein formulation. Specifically, as shown in Table 2, p55gag protein were inactive at concentrations of 10 μg, 25 μg and 50 μg. Further, as shown in Table 3, the SDS-PLG/p55 formulations were more active than the PVA-PLG/p55 and p55gag protein formulations, indicating that proteins were adsorbed more efficiently to the microparticles in the SDS-PLG/p55 formulations as compared to the PVA-PLG/p55 and p55gag protein formulations.

TABLE 2

PERCENT SPECIFIC LYSIS OF TARGETS

| Antigen Adjuvant (Adj. Dose) | Target Ratio | SvB$^a$ | SvB P7g+$^b$ | MC57 p7G-$^c$ |
|---|---|---|---|---|
| p55gag protein | 60 | 15 | 12 | 4 |
| (10 μg) | 15 | 11 | 8 | 3 |
|  | 4 | 7 | 6 | 3 |
| % Spon Release |  | 12 | 10 | 13 |
| p55gag protein | 63 | 10 | 18 | 2 |
| (25 μg) | 16 | 7 | 6 | −1 |
|  | 4 | 4 | 1 | −3 |
| % Spon Release |  | 12 | 10 | 13 |
| p55gag protein | 60 | 28 | 22 | 5 |
| (50 μg) | 15 | 13 | 12 | 2 |
|  | 4 | 9 | 3 | 3 |
| % Spon Release |  | 12 | 10 | 13 |
| p55gag protein | 60 | 8 | 50 | 0 |
| (10 μg) PLG/SDS | 15 | 5 | 21 | −3 |
| 0.6% 11.6 mg | 4 | 4 | 7 | −1 |
| % Spon Release |  | 12 | 10 | 13 |
| Vv gag/pol | 60 | 9 | 65 | 1 |
| (vaccinia virus | 15 | 4 | 38 | 1 |
| encoding gag) | 4 | 1 | 18 | 3 |
| % Spon Release | 12 | 10 | 10 | 13 |

$^a$SvB cell line without peptide pulsing
$^b$SvB cell line pulsed with p7g peptide
$^c$MC57 cell line pulsed with p7g peptide

TABLE 3

PERCENT SPECIFIC LYSIS OF TARGETS

| Effector | E:T Ratio | MC57$^a$ | MC57 + gag b$^b$ | SvB + gag b$^c$ |
|---|---|---|---|---|
| PVA-PLG/p55 | 60:1 | 8 | 15 | 11 |
| 10 μg | 12:1 | 3 | 10 | 2 |
|  | 2.4:1 | >1 | 5 | 2 |
| SDS-PLG/p55 | 60:1 | 6 | 35 | 4 |
| 10 μg | 12:1 | 3 | 12 | >1 |
|  | 2.4:1 | >1 | 3 | 2 |
| p55gag | 60:1 | 7 | 15 | 1 |
| protein 10 μg | 12:1 | 2 | 6 | 1 |
|  | 2.4:1 | >1 | 1 | >1 |

TABLE 3-continued

PERCENT SPECIFIC LYSIS OF TARGETS

| Effector | E:T Ratio | MC57$^a$ | MC57 + gag b$^b$ | SvB + gag b$^c$ |
|---|---|---|---|---|
| Vaccinia gag | 60:1 | >1 | 37 | >1 |
|  | 12:1 | >1 | 19 | >1 |
|  | 2.4:1 | 1 | 9 | >1 |

$^a$MC57 cell line without pulsing with peptide
$^b$MC57 cell line pulsed with gag b peptide
$^c$SVB cell line pulsed with gag b peptide Example 7

Preparation of pCMVgp120 DNA-Adsorbed Microparticles with Modified Surfaces

Microparticles with adsorbed plasmid DNA encoding gp120 were prepared as follows. 20 mg of blank microparticles, prepared as described in Examples 1 and 2, were incubated with increasing concentrations of pCMVgp120 DNA in a 1.0 ml volume for 3 hours at 4° C. Following incubation, the microparticles were centrifuged, washed twice with Tris-EDTA buffer and freeze-dried overnight. The microparticles were hydrolyzed as described in Example 5 and analyzed for the amount of adsorbed DNA at A$_{260}$ nm.

Table 4 illustrates the loading efficiency of PLG-PVA and PLG-CTAB microparticles. As indicated in the table, the PLG-CTAB microparticles adsorb more efficiently than the corresponding PLG-PVA particles.

TABLE 4

| Microparticle Type | Theoretical Load (% w/w) | Actual Load (% w/w) | Loading Efficiency (% w/w) |
|---|---|---|---|
| PLG-PVA | 1 | 0.44 | 44 |
| PLG-CTAB | 1 | 0.84 | 88 |
| PLG-PVA | 2 | 0.38 | 19 |
| PLG-CTAB | 2 | 1.23 | 62 |
| PLG-PVA | 3 | 0.33 | 11 |
| PLG-CTAB | 3 | 1.82 | 61 |
| PLG-PVA | 4 | 0.48 | 12 |
| PLG-CTAB | 4 | 2.36 | 59 |

Example 8

HCV-E2 Adsorption

Microparticles were prepared using PVA, and several different detergents, as described in the previous examples. E2 protein from Hepatitus C Virus (HCV) was adsorbed on the surface of the microparticles as follows: 0.2 mg/ml E2 was added to 20 mg of the microparticles in PBS to form a solution at 0.5% w/w E2/PLG in a total volume of 0.5 ml. The solutions were incubated for 1.5 hours at 37EC, then centrifuged. The supernatants were collected and then measured for protein content by microBCA. The results are shown in Table 5. The results confirm the superior adsorption of macromolecules by the microparticles of the present invention.

TABLE 5

| Microparticle Type | Protein | % bound (w/w E2/PLG) | % total E2 bound |
|---|---|---|---|
| PVA-PLG | E2 | 0.00 | 0.00 |
| CTAB-PLG | E2 | 0.43 | 96.00 |
| SDS-PLG | E2 | 0.14 | 31.00 |
| NaOleate-PLG | E2 | 0.36 | 81.00 |
| Pluronic P84-PLG | E2 | 0.00 | 0.00 |
| Pluronic L121-PLG | E2 | 0.00 | 0.00 |

Example 9

Adsorption of gp120 Protein

Microparticles were prepared using PVA as described in the previous examples. Microparticles were also prepared using NaOleate, an anionic detergent, as follows: a w/o/w emulsion was prepared with 1.67 ml of 30 mM NaCitrate at pH6 as the internal water phase, 16.7 ml of 6% polymer RG 505 PLG (Boehringer Ingelheim) in dichloromethane as the solvent (oil phase), and 66.8 ml of 0.4% NaOleate as the external aqueous phase. These microparticles appear in Table 6 below as "NaOleate-PLG (w/o/w)." Additionally, microparticles were prepared using NaOleate in an oil in water formulation, and these microparticles appear in Table 6 below as "NaOleate-PLG (o/w)." gp120 protein was adsorbed on the surface of the prepared microparticles as follows: 0.388 mg/ml of protein was added to about 20 mg of the microparticles in PBS to form a solution at about 1.4% w/w gp120/PLG in a total volume of 0.8 ml. The solutions were incubated for 1.5 hours at 37EC, then centrifuged. The supernatants were collected and then measured for protein content by microBCA. The results are shown in Table 6. The results confirm the superior adsorption of macromolecules by the microparticles of the present invention.

TABLE 6

| Microparticle Type | protein | % bound (w/w gp120/PLG) | % total E2 bound |
|---|---|---|---|
| PVA-PLG | gp120 | 0.01 | 0.00 |
| PVA-PLG | gp120 | 0.09 | 3.00 |
| NaOleate-PLG (w/o/w) | gp120 | 1.33 | 96.00 |
| NaOleate-PLG (w/o/w) | gp120 | 1.24 | 95.00 |
| NaOleate-PLG (o/w) | gp120 | 0.41 | 31.00 |
| NaOleate-PLG (o/w) | gp120 | 0.27 | 20.00 |
| NaOleate-PLG (o/w) | gp120 | 0.36 | 28.00 |
| NaOleate-PLG (o/w) | gp120 | 0.27 | 22.00 |
| NaOleate-PLG (o/w) | gp120 | 0.34 | 26.00 |
| NaOleate-PLG (o/w) | gp120 | 0.31 | 24.00 |
| NaOleate-PLG (o/w) | gp120 | −0.01 | −1.00 |
| NaOleate-PLG (o/w) | gp120 | −0.09 | −7.00 |

Example 10

Adsorption of Listeriolysin Protein

Microparticles were prepared using PVA and CTAB, as described in the previous examples. Listeriolysin protein (LLO) from *Listeria monocytogenes* was adsorbed on the surface of the microparticles as follows: 1.0 mg/ml LLO was added to 100 mg of the microparticles in PBS to form a solution at 1% w/w LLO/PLG in a total volume of 5 ml. The solutions were incubated for 1.5 hours at 37EC, then centrifuged. The supernatants were collected and then measured for protein content by microBCA. The results are shown in Table 7. The results confirm the superior adsorption of macromolecules by the microparticles of the present invention.

TABLE 7

| Microparticle Type | Protein | Targeted Load (% w/w) | Actual Load (% w/w) | Loading Efficiency |
|---|---|---|---|---|
| PVA-PLG | LLO | 0.10 | 0.10 | 100.0 |
| PVA-PLG | LLO | 0.25 | 0.08 | 32.0 |
| PVA-PLG | LLO | 0.50 | 0.12 | 24.0 |
| PVA-PLG | LLO | 1.00 | 0.18 | 18.0 |
| CTAB-PLG | LLO | 0.10 | 0.06 | 60.0 |
| CTAB-PLG | LLO | 0.25 | 0.19 | 76.0 |
| CTAB-PLG | LLO | 0.50 | 0.34 | 68.0 |
| CTAB-PLG | LLO | 1.00 | 0.71 | 71.0 |

Example 11

Effect of Aluminum Salt as an Adjuvant p55 gag DNA-adsorbed PLG microparticles were prepared as described above, using CTAB. The microparticles were injected intramuscularly in mice at two concentrations, and, as a control, DNA alone was injected at the same two concentrations. Additionally, in one trial, 50 μg aluminum phosphate was added to the injected CTAB composition. Each formulation was injected into ten mice. The mice were boosted after 28 days. Two weeks after the second immunization, serum was collected and the geometric mean titer (GMT) of each serum was measured, along with its standard error (SE). The results are summarized in Table 8, presented as both linear and log values. Each number is the average of the results obtained from the ten mice.

TABLE 8

| Formulation | GMT | SE | log GMT | log SE |
|---|---|---|---|---|
| DNA-CTAB 1 μg | 19546 | 5983 | 4.28 | 0.11 |
| DNA-CTAB 10 μg | 54487 | 5510 | 4.73 | 0.04 |
| DNA-CTAB 1 μg + ALUM 50 μg | 49765 | 10034 | 4.69 | 0.1 |
| DNA alone 1 μg | 10.6 | 2.7 | 1.01 | 0.07 |
| DNA alone 10 μg | 230 | 395 | 2.15 | 0.3 |

In order to compare these results statistically, P-values were generated for DNA-CTAB vs. DNA-CTAB+ALUM (P-value=0.0017); DNA-CTAB+ALUM vs. DNA alone (P-value<0.0001); and DNA-CTAB (10 μg) vs. DNA alone (10 μg) (P-value<0.0001). These P-values confirm the statistical significance of the values in Table 8.

Example 12

Measurement of Zeta Potentials

Measurement of zeta potentials was carried out on a DELSA 440 SX zetasizer from Coulter Corp., Miami, Fla. 33116. The system is calibrated using mobility standards from Coulter (EMP SL7, an aqueous suspension of polystyrene latex beads). Following rinsing of the sample cell with sterile water, samples are added to the sample cell. The counter is then set to zero by aligning the beam to its lowest value. The current is set at 0.7 mA for the reference and 20 V for the sample. Detector levels from all four beams are checked, then the sample is run by selecting "run" from the software, and frequency measurements are read. The beams should be 20 Hz apart. The mean zeta potential for each sample is then read.

Measurements for several microparticle formulations of the present invention were read, and the results are shown in Table 9. As the results indicate, absorbance of macromolecules to the microparticles' surfaces alters the zeta potentials of the microparticles.

TABLE 9

| Microparticle Type | Adherent macromolecule | Zeta Potential (mV) |
|---|---|---|
| PLG-PVA | none | −26 ± 8 |
| PLG-CTAB | none | +83 ± 22 |
| PLG-CTAB | p55 DNA | +35 ± 14 |
| PLG-SDS | none | −44 ± 26 |
| PLG-SDS | p55 protein | −32 ± 18 |
| PLG-Oleate | none | −64 ± 24 |
| PLG-Oleate | gp120 protein | −48 ± 14 |

Example 13

Microparticles with Encapsulated and Adsorbed Macromolecules (A). PLG microparticles were prepared using RG 505 PLG and PVA, and encapsulating the adjuvant LTK63. 100 mg of the microparticles was incubated with 5 ml PBS containing 400 μg/ml p24gag protein. The mixture was then incubated with rocking at room temperature overnight, washed by centrifugation with 20 ml PBS twice and with water once, then lyophilized. Following base hydrolysis and neutralization, the % adsorbed protein and % encapsulated adjuvant were measured; the results appear in Table 10.

(B). PLG microparticles were prepared using SDS and RG 505 PLG, and encapsulating adjuvant CpG oligonucleotides as follows: 5 ml of 6% RG505 polymer in DCM was emulsified with 0.5 ml of 5 mg/ml CpG in 50 mM Tris/EDTA, forming a w/o emulsion. The w/o emulsion was added to 20 ml of 1% SDS and then emulsified, forming a w/o/w emulsion. Microparticles were formed by solvent evaporation overnight, then washed, centrifuged, and lyophilized. 10 mg of the CpG-encapsulated microparticles was dissolved in 1 ml DCM. 0.5 ml water was added to extract the oligonucleotides, and the mixture was then centrifuged and the aqueous layer was injected on a size exclusion column with PBS as the mobile phase. 10 mg of placebo microparticles was mixed with 100 μg CpG oligonucleotides and extracted as above with DCM and run on the column as a standard. The amount of CpG oligonucleotides present in the entrapped particles was calculated against the standard.

p55gag was adsorbed on the CpG-encapsulated microparticles as follows: 50 mg of the lyophilized CpG-encapsulated microparticles was incubated overnight with 5 ml 25 mM Borate with 6M Urea (pH 9) containing 140 μg p55gag protein. The mixture was incubated with rocking overnight at room temperature, washed with 20 ml Borate buffer/6M Urea twice, and 20 ml water twice, then lyophilized.

10 mg of the CpG-encapsulated/p55gag adsorbed microparticles was base hydrolyzed, and measurements were taken of the % entrapped and % adsorbed macromolecules. The targeted load was 1.0%, except as otherwise indicated. The results appear in Table 10.

TABLE 10

| Microparticle Type | % encapsulated (w/w) | % adsorbed (w/w) |
|---|---|---|
| (A). PLG-PVA LTK63 encapsulated p24gag adsorbed | 0.46 | 1.2* |
| (B). PLG-SDS CpG encapsulated p55gag adsorbed | 0.41 | 1.0 |

*targeted load = 2.0%

Example 14

Microparticles with Two Adsorbed Macromolecules (A). According to the present invention, two or more macromolecules may be administered in a composition comprising microparticles which have adsorbed both macromolecules, or may be administered in a composition comprising two or more distinct microparticles, each having adsorbed a single macromolecule. For example, microparticles were prepared adsorbing both E2 polypeptide and adjuvant CpG oligonucleotides as follows: Blank PLG-CTAB were prepared as previously described. 20 mg of the lyophilized microparticles were incubated for 4 hours with 1 ml of 200 μg/ml E2 in saline. The mixture was rocked at room temperature for 4 hours, washed with 20 ml of normal saline water twice by centrifugation at 10,000 G, and the pellet was resuspended in 1 ml of a CpG solution in TE buffer containing 200 μg/ml CpG for 4 hours at room temperature. The final suspension was washed twice with TE buffer by centrifugation, and then lyophilized. 10 mg of the microparticles with adsorbed CpG and E2 was base hydrolyzed and protein concentration was determined by BCA, and the residual amount of CpG in the supernatant was assayed by HPLC to measure the amount of CpG adsorbed on the microparticles. The results appear in Table 11, demonstrating positive adsorption for both macromolecules.

(B). Microparticles were prepared according to the invention. A portion were used to adsorb E2 polypeptide, while another portion was used to adsorb adjuvant CpG oligonucleotides. Blank PLG-CTAB were prepared as previously described. 20 mg of the lyophilized microparticles were incubated for 4 hours with 1 ml of 200 μg/ml E2 in saline. The mixture was rocked at room temperature for 4 hours, washed with 20 ml of normal saline water twice by centrifugation at 10,000 G, then lyophilized. Separately, 20 mg of the lyophilized microparticles were incubated for 4 hours with 1 ml of 200 μg/ml CpG in TE buffer. The mixture was rocked at room temperature for 4 hours, washed with 20 ml of TE buffer twice by centrifugation at 10,000 G, then lyophilized. Results of measurements of the percent adsorbed macromolecules appears in Table 11.

TABLE 11

| Microparticle Type | % adsorbed E2 (w/w)* | % adsorbed CpG (w/w)* |
|---|---|---|
| (A). PLG-SDS E2 adsorbed CpG adsorbed | 0.71 | 0.32 |
| (B). PLG-SDS E2 adsorbed | 0.64 | n/a |
| (B). PLG-SDS CpG adsorbed | n/a | 0.81 |

*targeted load = 1.0%

Example 15

Microparticles Formed Using Combination of Detergent and PVA

The following procedure was used to form microparticles comprising two surfactants: PVA and a detergent: 10 ml of 5% PLG polymer and 0.2% of the detergent DOTAP in DCM were emulsified at 12,000 rpm for 3 minutes with 1.0 ml distilled water to form the primary w/o emulsion. The w/o emulsion was added to 40 ml of 0.8% PVA and emulsified for 3 minutes to form the second w/o/w emulsion, which was stirred overnight to evaporate the solvent, and microparticles were formed. The microparticles were washed twice in distilled water and lyophilized. The microparticles are then ready for adsorption of macromolecules in accordance with the present invention.

The same procedure was employed to form microparticles comprising a combination of PVA and the detergent DDA.

Example 16

Immunogenicity of Microparticles With Adsorbed p55 DNA

Microparticles were formed as in the previous examples using the detergents CTAB or DDA. p55 DNA was adsorbed to the microparticles and immunogenicity was assessed using the procedures described in in the previous examples. The results are summarized in Table 12 below.

TABLE 12

| PERCENT SPECIFIC LYSIS OF TARGETS | | |
|---|---|---|
| Effector | E:T Ratio | Sv/B P7g[a] |
| PLG-CTAB/ | 60:1 | 71 |
| p55 DNA | 15:1 | 55 |
| 1 µg | 4:1 | 31 |
| PLG-DDA/ | 60:1 | 70 |
| p55 | 15:1 | 54 |
| 1 µg | 4:1 | 17 |
| p55 DNA alone | 60:1 | 3 |
| 1 µg | 15:1 | 1 |
|  | 4:1 | 0 |
| Vaccinia gag | 60:1 | 64 |
| 2 × 10[7] pfu | 15:1 | 35 |
|  | 4:1 | 11 |

[a]SVB cell line pulsed with gag b peptide

Example 17

In-Vivo Luciferase Expression Using Microparticles With Adsorbed Luciferase DNA Microparticles were formed using the above-described procedures using PLG and the detergent CTAB. Luciferase DNA was adsorbed thereon using the methods previously described. In vitro luciferase expression using a 5 µg dose of luciferase DNA was measured using the luciferase DNA alone (1248 pg) and the microparticles with luciferase DNA adsorbed thereon (2250 pg). In vivo luciferase expression was measured in muscle on days 1 and 14 following administration as follows: Two groups of mice (n=5) were each injected with either 50 µg of Luciferase plasmid or 50 µg of PLG-CTAB-Luciferase DNA microparticles. Both groups of mice were injected intramuscularly in the anterior tibialis (TA) muscle on two legs. Both TA muscles from each mouse in the two groups were harvested either at day 1 or day 14 and stored in a −80 C freezer. The muscles were ground with a mortar and pestle on dry ice. The powdered muscles were collected in eppendorf tubes with 0.5 ml of 1× Reporter Lysis Buffer. The samples were vortexed for 15 minutes at room temperature. After freeze/thawing 3×, the samples were spun at 14,000 rpm for 10 minutes. The supernatant of the TA muscles of each mice at each timepoint were pooled and 20 ul of the samples were assayed using an ML3000 (Dynatech) under enhanced flash for Luciferase expression.

Luciferase determination was performed using a chemiluminiscence assay. The buffer was prepared containing 1 mg/ml of BSA in 1× Reporter Lysis (Promega). The luciferase enzyme stock (Promega) at 10 mg/ml was used as a standard, diluted to a concentration of 500 pg/20 ul. This standard was serially diluted 1:2 down the Microlite 2 plate (Dynatech) to create a standard curve. 20 µl of the blank and the samples were also placed on the plate and were serially diluted 1:2. The plates were placed in the ML3000 where 100 ul of the Luciferase Assay Reagent (Promega) were injected per well. Under enhanced flash, the relative light units were measured for each sample.

The results are tabulated below in Table 13.

TABLE 13

| Microparticle Type | In vivo luciferase expression Day 1 (pg) | In vivo luciferase expression Day 14 (pg) |
|---|---|---|
| PLG-CTAB Luciferase DNA adsorbed (50 ug) | 9.51 | 44.95 |
| Luciferase DNA alone (50 ug) | 6.78 | 9.29 |

Example 18

Immunogenicity of Microparticles with Adsorbed vs. Entrapped Antigen

Microparticles were prepared using the procedures discussed in the previous examples. E2 protein was then adsorbed thereon as described above. Microparticles were also prepared with E2 entrapped therein, rather than adsorbed thereon, as described above. The microparticles were assessed for their ability to induce IgG antibodies following immunization of 10 mice with each type of microparticle. The geometric mean titer (GMT) of serum from each mouse was measured, then averaged for the group of 10 animals. Standard error (SE) was also calculated. Fisher's PLSD (significance level 5%) was measured at p=0.0006. The results are shown in Table 14 below: The results clearly demonstrate superior induction of humoral immune response using the adsorbed microparticles of the present invention.

TABLE 14

| Formulation | GMT | SE |
|---|---|---|
| PLG with entrapped E2 | 293 | 270 |
| PLG with adsorbed E2 | 3122 | 1310 |

Example 19

Immunogenicity of Microparticles with HCV E1E2 Protein Adsorbed Thereon

PLG-CTAB microparticles were prepared using the procedures discussed in the previous examples. E1E2 protein from Hepatitis C Virus (HCV) was adsorbed thereon. The particles were used to immunize mice, with or without the adjuvant Alum, in dosages of microparticles calculated to provide either 10 µg or 100 µg of protein. Geometric mean titer was measured, and the results are shown below in Table 15.

TABLE 15

| Formulation | GMT | SE |
|---|---|---|
| PLG/CTAB E1E2 (10 µg) | 4117 | 558 |
| PLG/CTAB E1E2 (100 µg) | 7583 | 659 |
| PLG/CTAB E1E2 Alum (10 µg) | 3356 | 436 |
| PLG/CTAB E1E2 Alum (100 µg) | 10485 | 1548 |
| HCV E1E2 DNA (10 µg) | 87 | 63 |
| HCV E1E2 DNA (100 µg) | 7621 | 571 |

As the results indicate, the microparticles with protein adsorbed thereon produce a superior immune response at the 10 µg dose. This demonstrates that the microparticles have the advantage of being useful in eliciting immune responses at low doses where free DNA is unable to generate such responses.

Example 20

Immunogenicity of Microparticles with Adsorbed p24 gag protein

PLG-PVA microparticles were prepared using the procedures discussed in the previous examples. The protein p24 gag was then adsorbed thereon as described above. The microparticles were assessed for their ability to induce IgG, IgG1, and IgG2a antibodies following immunizations of 10 mice. The geometric mean titer (GMT) of serum collected from the mice 2 weeks post $2^{nd}$ immunization (2wp2) and 2 weeks post $3^{rd}$ immunization (2wp3) were measured, then averaged for the group of 10 animals. Standard error (SE) was also calculated. The results are shown in Table 16 below: The results clearly demonstrate superior induction of humoral immune response using the adsorbed microparticles of the present invention.

TABLE 16

| | IgG GMT | IgG SE | IgG1 GMT | IgG1 SE | IgG2a GMT | IgG2a SE |
|---|---|---|---|---|---|---|
| PLG-PVA/p24 gag (2wp2) | 5813.59 | 2400.58 | 3741.17 | 2039.08 | 755.3 | 587.21 |
| p24 gag alone (2wp2) | 6.6 | 7.91 | 6.51 | 6.85 | 5 | 1 |
| PLG-PVA/p24 gag (2wp3) | 26730.29 | 3443.67 | 40088.65 | 8989.07 | 6974.22 | 1457.74 |
| p24 gag alone (2wp3) | 7.15 | 5.59 | 8.22 | 12.3 | 5 | 1 |

Example 21

IM Immunization of p55 gag Protein and Various Adjuvants

PLG/CTAB, PLG/SDS, and PLG/PVA microparticles were formed as described above in the previous examples. Eight groups of microparticles were made in order to analyze the different effects of immunizing mice with adsorbed antigen p55 gag protein on microparticles vs. providing free soluble p55 gag, and to determine the effects of having the adjuvant CpG (20 base long single stranded oligonucleotides with a CpG motif) also adsorbed on other microparticles or provided in free soluble form. The different groups were prepared as follows:

Group 1 used soluble p55 gag protein (recombinant HIV p55 gag protein produced in yeast at 2 mg/ml in tris/NaCl buffer with 2M urea) mixed with PLG/CTAB particles with adsorbed CpG.

Group 2 used PLG/SDS particles with adsorbed p55 gag mixed with PLG/CTAB particles with adsorbed CpG.

Group 3 used PLG/SDS particles with adsorbed p55 gag mixed with free CpG.

Group 4 used PLG/SDS particles with adsorbed p55 gag and no adjuvant.

Group 5 used PLG/PVA particles with p55 gag entrapped therein mixed with PLG/CTAB particles with CpG adsorbed.

Group 6, a control, used no antigen, and soluble CpG.

Group 7, another control, used soluble p55 gag protein and no adjuvants.

Group 8, another control, used only vaccinia virus (vv gag) expressing the gag gene, and no adjuvants.

For each group, 10 mice were immunized with sufficient quantities of microparticles or free molecules such that the dosage of p55 gag antigen and CpG adjuvant were 25 µg each (if present in the group), except for Group 8 which was used at a dosage of 10×10⁷ pfu. The route of immunization was IM, except for Group 8, which route was IP. Following immunization, serum anti-p55 IgG titer was measured, the results of which appear below in Table 17A (3wp2, three weeks post second immunization). Table 17B provides analysis of the isotypes IgG1 and IgG2a components, including the ratio of IgG2A/IgG1. Lysis of targets by CTL was also measured with each group, the results of which appear below in Tables 18A and 18B (two separate experiments).

TABLE 17A

Serum IgG Titer

| Group | Form of p55 gag Protein Antigen | Form of CpG Adjuvant | Serum Titer |
|---|---|---|---|
| 1 | soluble | adsorbed on PLG/CTAB particles | 43250 |
| 2 | adsorbed on PLG/SDS particles | adsorbed on PLG/CTAB particles | 49750 |
| 3 | adsorbed on PLG/SDS particles | Soluble | 62750 |
| 4 | adsorbed on PLG/SDS particles | None | 7550 |

TABLE 17A-continued

Serum IgG Titer

| Group | Form of p55 gag Protein Antigen | Form of CpG Adjuvant | Serum Titer |
|---|---|---|---|
| 5 | entrapped within PLG/PVA particles | adsorbed on PLG/CTAB particles | 127000 |
| 6 | soluble | Soluble | 38 |
| 7 | soluble | None | 2913 |
| 8 | vaccinia virus (vv gag) | None | 938 |

TABLE 17B

|  | IgG GMT | IgG1 GMT | IgG2a GMT | IgG2a/IgG1 |
|---|---|---|---|---|
| PLG/CTAB-CpG plus soluble p55 | 43,250 | 18,750 | 17,500 | 0.9333 |
| PLG/CTAB-CpG plus PLG/SDS-p55 | 49,750 | 24,750 | 24,500 | 0.9899 |
| PLG/SDS-p55 plus free CpG | 62,750 | 30,000 | 32,500 | 1.0833 |
| PLG/SDS-p55 with no CpG | 7,550 | 18,600 | 350 | 0.0188 |
| PLG/CTAB-CpG plus PLG/PVA with entrapped p55 | 127,000 | 72,750 | 49,250 | 0.6770 |
| Free CpG1 | 38 | Not detectable | 25 | — |
| No adjuvant | 2913 | 7,450 | 88 | 0.0117 |
| vv gag, no adjuvant | 938 | 488 | 375 | 0.7692 |

TABLE 18A

PERCENT SPECIFIC LYSIS OF TARGETS

| Group | Form of p55 gag Protein Antigen | Form of CpG Adjuvant | Target Ratio | SvB pGAG[a] | SvB P7g+[b] |
|---|---|---|---|---|---|
| 1 | soluble | adsorbed on PLG/CTAB particles | 60 | 3 | 41 |
|  |  |  | 15 | 0 | 15 |
|  |  |  | 4 | -1 | 8 |
| 2 | adsorbed on PLG/SDS particles | adsorbed on PLG/CTAB particles | 60 | 7 | 77 |
|  |  |  | 15 | 4 | 49 |
|  |  |  | 4 | 2 | 26 |
| 3 | adsorbed on PLG/SDS particles | soluble | 60 | 6 | 51 |
|  |  |  | 15 | 3 | 30 |
|  |  |  | 4 | 4 | 11 |
| 4 | adsorbed on PLG/SDS particles | none | 60 | 4 | 48 |
|  |  |  | 15 | 2 | 21 |
|  |  |  | 4 | 1 | 7 |
| 5 | entrapped within PLG/PVA particles | adsorbed on PLG/CTAB particles | 60 | 3 | 37 |
|  |  |  | 15 | 2 | 17 |
|  |  |  | 4 | 0 | 4 |
| 6 | soluble | soluble | 60 | 4 | 23 |
|  |  |  | 15 | 4 | 7 |
|  |  |  | 4 | 2 | 3 |
| 7 | soluble | none | 60 | 1 | 4 |
|  |  |  | 15 | -1 | 1 |
|  |  |  | 4 | 0 | 2 |
| 8 | vaccinia virus (vv gag) | none | 60 | 3 | 52 |
|  |  |  | 15 | 2 | 25 |
|  |  |  | 4 | 3 | 16 |

[a] SvB cell line pulsed with irrelevant peptide
[b] SvB cell line pulsed with p7g peptide

TABLE 18B

PERCENT SPECIFIC LYSIS OF TARGETS

| Group | Form of p55 gag Protein Antigen | Form of CpG Adjuvant | Target Ratio | SvB pGAG[a] | SvBP7g+[b] |
|---|---|---|---|---|---|
| 1 | soluble | adsorbed on PLG/CTAB particles | 60 | 0 | 47 |
|  |  |  | 15 | -1 | 23 |
|  |  |  | 4 | 0 | 13 |
| 2 | adsorbed on PLG/SDS particles | adsorbed on PLG/CTAB particles | 60 | 3 | 68 |
|  |  |  | 15 | 2 | 48 |
|  |  |  | 4 | 3 | 16 |
| 3 | adsorbed on PLG/SDS particles | soluble | 60 | 2 | 32 |
|  |  |  | 15 | 1 | 17 |
|  |  |  | 4 | 1 | 0 |
| 4 | adsorbed on PLG/SDS particles | none | 60 | 1 | 27 |
|  |  |  | 15 | 2 | 19 |
|  |  |  | 4 | 2 | 3 |
| 5 | entrapped within PLG/PVA particles | adsorbed on PLG/CTAB particles | 60 | 0 | 31 |
|  |  |  | 15 | 0 | 13 |
|  |  |  | 4 | -1 | 3 |
| 6 | soluble | soluble | 60 | 3 | 17 |
|  |  |  | 15 | 1 | 4 |
|  |  |  | 4 | 1 | 0 |
| 7 | soluble | none | 60 | -1 | 10 |
|  |  |  | 15 | -1 | 1 |
|  |  |  | 4 | 4 | 2 |
| 8 | vaccinia virus (vv gag) | none | 60 | 1 | 48 |
|  |  |  | 15 | 1 | 23 |
|  |  |  | 4 | 1 | 12 |

[a] SvB cell line pulsed with irrelevant peptide
[b] SvB cell line pulsed with p7g peptide

Example 22

IM Immunization of p55 gag Protein or p55 DNA and Various Adjuvants

PLG microparticles were formed as described above in the previous. Groups of microparticles were made in order to analyze the different effects of immunizing mice with adsorbed antigen p55 gag protein on microparticles vs. providing free soluble p55 gag, and to determine the effects of having the adjuvant CpG (CpG1 or CpG2, representing different groups of oligonucleotides) also adsorbed on other microparticles or provided in free soluble form. Ten groups of animals were immunized with different formulations as follows:

Group 1 used PLG/CTAB particles with adsorbed CpG1 mixed with free p55 gag protein (recombinant HIV p55 gag protein produced in yeast at 2 mg/ml in tris/NaCl buffer with 2M urea).

Group 2 used PLG/CTAB particles with adsorbed CpG1 mixed with PLG/SDS particles with adsorbed p55 gag protein.

Group 3 used PLG/SDS particles with adsorbed p55 gag protein mixed with free CpG1.

Group 4 used PLG/SDS particles with adsorbed p55 gag protein and no adjuvant.

Group 5 used PLG/CTAB particles with adsorbed CpG1 and entrapped PVA/p55 gag protein.

Group 6, PLG/CTAB particles with adsorbed CpG2 mixed with PLG/SDS particles with adsorbed p55 gag protein.

Group 7, a control, used PLG/SDS particles with adsorbed p55 gag protein and blank PLG/CTAB microparticles.

Group 8, another control, used only free CpG2.

Group 9, another control, used only free CpG1.

Group 10, another control, used only free soluble p55 gag protein.

For each group, 10 mice were immunized with sufficient quantities of microparticles or free molecules such that the dosage of p55 gag antigen and CpG adjuvant were 25 μg each (if present in the group. The route of immunization was IM TA. Following immunization, serum anti-p55 IgG titer was measured, the results of which appear below in Table 19A. The serum was measured at 2wp2 (two weeks post second immunization) and 2wp3 (two weeks post third immunization).

TABLE 19A

Serum IgG Titer

| Group | Form of p55 gag Protein Antigen | Form of CpG Adjuvant | Serum Titer [GMT/(SE)] 2wp2 | 2wp3 |
|---|---|---|---|---|
| 1 | soluble | adsorbed on PLG/CTAB particles | 40,200 (7973) | 120,000 (13600) |
| 2 | adsorbed on PLG/SDS particles | adsorbed on PLG/CTAB particles | 56,500 (9495) | 146,000 (24700) |
| 3 | adsorbed on PLG/SDS particles | soluble | 53,000 (13900) | 108,000 (14900) |
| 4 | adsorbed on PLG/SDS particles | none | 7,536 (1628) | 1,628 (3218) |
| 5 | entrapped within PLG/PVA particles | adsorbed on PLG/CTAB particles | 126,000 (12900) | 201,000 (24400) |
| 6 | Adsorbed on PLG/SDS particles | Adsorbed on PLG/CTAB particles | 4,684 (814) | 62,100 (11300) |
| 7 | Adsorbed on PLG/SDS particles | none | 24,600 (4456) | 53,900 (7451) |
| 8 | none | soluble | 82 (1308) | 2,415 (1874) |
| 9 | none | soluble | 57 (31) | 12,200 (4306) |
| 10 | none | none | 6,338 (999) | 15,900 (2929) |

A similar experiment was performed using various PLG microparticles, using CTAB as the detergent, using p55 gag DNA as the antigen, using CpG or LTK63 as the adjuvant, and using the following groups:

Group 1 used PLG/PVA/CTAB particles with adsorbed p55 gag DNA at 1 μg.

Group 2 used PLG/PVA/CTAB particles with adsorbed p55 gag DNA at 10 μg.

Group 3 used PLG/CTAB particles with adsorbed p55 gag DNA at 1 μg.

Group 4 used PLG/CTAB particles with adsorbed p55 gag DNA at 10 μg.

Group 5 used soluble p55 gag DNA at 1 μg without particles or adjuvants.

Group 6 used soluble p55 gag DNA at 10 μg without particles or adjuvants.

Group 7 used PLG/CTAB particles with adsorbed p55 gag DNA at 1 μg mixed with free CpG.

Group 8 used PLG/CTAB particles with adsorbed p55 gag DNA at 1 μg mixed with PLG/CTAB particles with adsorbed CpG1.

Group 9 used PLG/CTAB particles with adsorbed p55 gag DNA at 1 μg mixed with free LTK63.

Group 10 used PLG/CTAB particles with adsorbed p55 gag DNA at 1 μg mixed with PLG/SDS particles with adsorbed LTK63.

For each group, 10 mice were immunized with sufficient quantities of microparticles or free molecules such that the dosage of p55 DNA antigen was as indicated, and CpG adjuvant was 25 μg each (if present in the group). The route of immunization was 1M TA. Following immunization, serum anti-p55 IgG titer was measured, the results of which appear below in Table 19B. The serum was measured at 2wp2 (two weeks post second immunization).

TABLE 19B

Serum IgG Titer

| Group | Form of p55 gag DNA Antigen | Form of Adjuvant | Serum Titer [GMT/(SE)] |
|---|---|---|---|
| 1 | Adsorbed on PLG/PVA/CTAB particles | none | 22,900 (8892) |
| 2 | Adsorbed on PLG/PVA/CTAB particles | none | 81,700 (8578) |
| 3 | Adsorbed on PLG/CTAB particles | none | 18,100 (12800) |
| 4 | Adsorbed on PLG/CTAB particles | none | 101,000 (10900) |
| 5 | soluble | none | 14 (130) |
| 6 | soluble | none | 1,060 (1905) |
| 7 | Adsorbed on PLG/CTAB particles | soluble CpG | 50,400 (19700) |
| 8 | Adsorbed on PLG/CTAB particles | CpG adsorbed on PLG/CTAB particles | 68,300 (9534) |
| 9 | Adsorbed on PLG/CTAB particles | soluble LTK63 | 109,000 (15900) |
| 10 | Adsorbed on PLG/CTAB particles | LTK63 adsorbed on PLG/SDS particles | 52,900 (9229) |

A similar experiment was performed using various PLG microparticles, or MF59 microemulsions, using phosphatidic acid (PA), DSS, DOTAP, or CTAB as the detergent, using gp120 protein as the antigen, and using the following groups:

Group 1 used MF59 emulsion with free gp120 protein.

Group 2 used MF59/PA emulsion with adsorbed gp120 protein.

Group 3 used PLG/PVA particles with entrapped gp120.

Group 4 used PLG/DSS particles with adsorbed gp120 protein and no adjuvant.

Group 5 used PLG/DSS particles with adsorbed gp120 protein and PLG/CTAB particles with CpG adsorbed thereon.

Group 6 used PLG/CTAB particles with adsorbed CpG.

Group 7 used PLG/DSS particles with adsorbed gp120 protein mixed with MF59/DOTAP 80 particles with adsorbed CpG1.

Group 8 used MF59/DOTAP 80 emulsion with adsorbed CpG1.

Group 9 used PLG/CTAB particles with adsorbed CpG mixed with MF59/PA particles with adsorbed gp120 protein.

Group 10 used free CpG1 plus soluble gp120 protein.

For each group, 10 mice were immunized with sufficient quantities of microparticles or free molecules such that the dosage of gp120 gag antigen and CpG adjuvant were 25 μg each (if present in the group). The route of immunization was 1M TA. Following immunization, serum anti-gp120 IgG titer was measured, the results of which appear below in Table 19C. The serum was measured at 2wp2 (two weeks post second immunization) and 2wp3 (two weeks post third immunization).

TABLE 19C

Serum IgG Titer

| Group | Form of gp120 gag Protein Antigen | Form of CpG Adjuvant | Serum Titer [GMT/(SE)] 2wp2 | 2wp3 |
|---|---|---|---|---|
| 1 | Soluble in MF59 | none | 2,995 (679) | 7,797 (864) |
| 2 | adsorbed on MF59/PA emulsion | none | 997 (201) | 4,383 (820) |
| 3 | entrapped in PLG/PVA particles | none | 740 (307) | 3,655 (569) |
| 4 | adsorbed on PLG/DSS particles | none | 530 (145) | 1,306 (306) |
| 5 | adsorbed on PLG/DSS particles | adsorbed on PLG/CTAB particles | 6,835 (2217) | 26,294 (3972) |
| 6 | none | Adsorbed on PLG/CTAB particles | 9 (6) | 127 (143) |
| 7 | adsorbed on PLG/DSS particles | adsorbed on MF59/DOTAP emulsion | 16,588 (4997) | 26,688 (6583) |
| 8 | none | adsorbed on MF59/DOTAP emulsion | 1,050 (978) | 5,216 (2379) |
| 9 | Adsorbed on MF59/PA particles | Adsorbed on PLG/CTAB particles | 81 (1530) | 2012 (7234) |
| 10 | Soluble | soluble | 8 (37) | 15 (163) |

The above data demonstrates that in the case of gp120 protein antigen, the best immune responses were elicited in the group immunized with antigen adsorbed to PLG particles, whether the CpG oligonucleotides were adsorbed on other PLG particles or MF59/DOTAP emulsion. In contrast, where the antigen was adsorbed on the MF59/DOTAP emulsion and the CpG oligonucleotides were adsorbed on PLG particles, the immune response was essentially insignificant. Equipped with the teachings herein, one of skill in the art may readily determine which combination of adsorbed microparticle and/or microemulsion is best-suited for any particular antigen.

Example 23

Adsorption and Entrapment of p55 DNA

PLG/CTAB microparticles with adsorbed p55 DNA were formed as described above in the previous examples, and tested for antibody induction at four weeks post IM immunization, and two weeks post second IM immunization versus blank particles, free CTAB, and free p55 DNA. The results appear below in Table 20A, and show the clear advantage of having p55 DNA adsorbed on microparticles rather than free in solution.

TABLE 20A

| Formulation | 4wp1 GMT | 4wp1 SE | 2wp2 GMT | 2wp2 SE |
|---|---|---|---|---|
| PLG/CTAB with p55 DNA adsorbed (1 µg) | 27 | 85 | 17,800 | 9156 |

TABLE 20A-continued

| Formulation | 4wp1 GMT | 4wp1 SE | 2wp2 GMT | 2wp2 SE |
|---|---|---|---|---|
| Free CTAB(1 µg) | 8 | 25 | 181 | 653 |
| Blank PLG (1 µg) | 4 | 2 | 32 | 106 |
| Blank PLG + free CTAB (1 µg) | 6 | 25 | 71 | 1631 |
| Free p55 DNA (1 µg) | 3 | 0 | 69 | 60 |

CTL induction was examined with the same formulations, and was measured at 3 weeks post first immunization, using target to effector ratios of 4:1, 15:1, and 60:1. The results appear below in Table 20B, showing the advantage of p55 DNA adsorbed on microparticles.

TABLE 20B

PERCENT SPECIFIC LYSIS OF TARGETS

| Formulation | E:T Ratio | lysis |
|---|---|---|
| PLG/CTAB-p55 DNA(1 µg) | 60:1 | 33 |
| | 15:1 | 11 |
| | 4:1 | 1 |
| Free CTAB | 60:1 | −1 |
| | 15:1 | 1 |
| | 4:1 | 0 |
| Blank PLG | 60:1 | 12 |
| | 15:1 | 2 |
| | 4:1 | 3 |
| Blank PLG + CTAB | 60:1 | 18 |
| | 15:1 | 6 |
| | 4:1 | 3 |
| Free p55 DNA (1 µg) | 60:1 | 3 |
| | 15:1 | 0 |
| | 4:1 | 0 |
| vv gag(2 × 107 pfu) | 60:1 | 59 |
| | 15:1 | 24 |
| | 4:1 | 9 |

PLG/CTAB microparticles with adsorbed p55 DNA, and PLG/PVA microparticles with p55 DNA entrapped within, were formed as described above in the previous examples. IM immunization of mice and antibody induction (collection and analysis of serum) were performed as described in the previous examples, at four weeks post $1^{st}$ immunization (4wp1), and 2, 4, 6, 13, and 15 weeks post $2^{nd}$ immunization (2wp2, 4wp2, 6wp2, 13wp2, and 15wp2 respectively). The results, shown in Table 20C below, demonstrate a clear advantage of the adsorbed microparticles over both entrapped and free p55.

TABLE 20C

| Formulation | 4wp1 | 2wp2 | 4wp2 | 6wp2 | 13wp2 | 15wp2 |
|---|---|---|---|---|---|---|
| PLG/CTAB with p55 DNA adsorbed (1 µg) | 576 | 79300 | 156000 | 227000 | 988000 | 123000 |
| PLG/PVA with p55 DNA entrapped(1 µg) | 996 | 1915 | 2215 | 1376 | 25100 | 1084 |
| p55 plasmid alone (1 µg) | 912 | 1149 | 1360 | 701 | 1075 | 742 |
| p55 plasmid alone (10 µg) | 1489 | 10700 | 7885 | 26300 | 31600 | 17300 |

PLG/CTAB/PVA particles with adsorbed p55 DNA (1% DNA) were prepared as described in previous examples, and measured for several characteristics, the results appear below in Table 20D.

TABLE 20D

| CTAB % w/v | PVA % w/v | p55 DNA Target Load | p55 DNA Actual Load | Loading Efficiency (%) | Mean Size (μm) | Zeta Potential without DNA (mV) | Zeta Potential with DNA (mV) | Residual CTAB after 4 washes (% w/w) |
|---|---|---|---|---|---|---|---|---|
| 0.2 | 0.8 | 1.0 | 0.74 | 74 | 1.86 | 46 ± 14 | 24 ± 14 | 0.42 |

PLG/CTAB and PLG/PVA/CTAB particles were prepared as previously described, and p55 DNA was adsorbed thereon. Mice were immunized with particles such that the dosage of p55 DNA was either 1 μg or 10 μg. The results of an antibody induction experiment 2 weeks post $2^{nd}$ immunization appeared above in Table 19B, and are summarized below in Table 20E.

TABLE 20E

| Formulation | 2wp2 GMT | 2wp2 SE |
|---|---|---|
| PLG/PVA/CTAB with p55 DNA adsorbed (1 μg) | 22,900 | 8,892 |
| PLG/PVA/CTAB with p55 DNA adsorbed (10 μg) | 81,700 | 8,578 |
| PLG/CTAB with p55 DNA adsorbed (1 μg) | 18,100 | 12,800 |
| PLG/CTAB with p55 DNA adsorbed (10 μg) | 101,000 | 10,900 |
| Free p55 DNA (1 μg) | 14 | 130 |
| Free p55 DNA (10 μg) | 1,060 | 1,905 |

Various PLG microparticles, or MF59 microemulsions, using DOTAP or CTAB as the detergent, and using p55 DNA as the antigen, were prepared and used to immunize mice as follows:

Group 1 used PLG/CTAB particles with adsorbed p55 DNA.

Group 2 used PLG/CTAB particles with entrapped p55 DNA.

Group 3 used PLG/DOTAP particles with adsorbed p55 DNA.

Group 4 used PLG particles with free CTAB and free p55 DNA.

Group 5 used MF59/DOTAP 80 emulsion with free p55 DNA.

Group 6 used MF59 emulsion with free p55 DNA.

Group 7 used free p55 DNA alone.

Group 8 used blank PLG particles and free p55 DNA.

Group 9 used blank PLG particles, free CTAB, and free p55 DNA.

For each group, 10 mice were immunized with sufficient quantities of microparticles or free molecules such that the dosage of p55 DNA was 1 μg. The route of immunization was IM TA. Following immunization, serum anti-p55 DNA titer was measured, the results of which appear below in Table 20F. The serum was measured at 3wp1 (three weeks post first immunization) and 3wp2 (three weeks post second immunization).

TABLE 20F

| | Form of p55 | Serum IgG Titer | |
|---|---|---|---|
| | | Serum Titer [GMT/(SE)] | |
| Group | DNA Antigen | 3wp1 | 3wp2 |
| 1 | adsorbed on PLG/CTAB particles | 72 (29) | 21,600 (18,400) |
| 2 | entrapped in PLG/CTAB particles | 148 (95) | 20,200 (3048) |
| 3 | adsorbed on PLG/DOTAP particles | 40 (52) | 23,800 (2293) |
| 4 | free | 5 (3) | 7 (30) |
| 5 | adsorbed on MF59/DOTAP emulsion | 96 (7) | 31,000 (3267) |
| 6 | adsorbed on MF59 emulsion | 5 (0) | 10 (19) |
| 7 | free | 3 (0) | 3 (0) |
| 8 | free | 3 (0) | 5 (2) |
| 9 | free | 3 (0) | 35 (55) |

PLG/CTAB and PLG microparticles, and MF59 microemulsions using DOTAP 40 or DOTAP 80 and using p55 DNA as the antigen at a dosage of 1 μg except where indicated otherwise, were prepared as previously described, and used to immunize mice as follows:

Group 1 used PLG/CTAB particles with adsorbed p55 DNA, burst free (i.e., which particles were burst in vitro prior to immunization).

Group 2 used PLG/CTAB particles with adsorbed p55 DNA.

Group 3 used PLG/CTAB particles (non-freeze dried) with adsorbed p55 DNA.

Group 4 used MF59/DOTAP 40 emulsion with adsorbed p55 DNA.

Group 5 used MF59/DOTAP 40 emulsion with adsorbed p55 DNA, at a dosage of 10 μg.

Group 6 used MF59/DOTAP 80 emulsion with adsorbed p55 DNA.

Group 7 used MF59/DOTAP 80 emulsion with adsorbed p55 DNA, at a dosage of 10 μg.

Group 8 used free p55 DNA.

Group 9 used free p55 DNA at a dosage of 10 μg.

Group 10 used MF59 emulsion with free p55 DNA at a dosage of 10 μg.

For each group, 10 mice were immunized with sufficient quantities of microparticles or free molecules such that the dosage of p55 DNA was 1 or 10 μg, as indicated. The route of immunization was IM TA. Following immunization, serum anti-p55 DNA titer was measured, the results of which appear below in Table 20G. The serum was measured at 4wp1 (four weeks post first immunization) and 2wp2 (two weeks post second immunization).

TABLE 20G

| | | Serum IgG Titer | |
|---|---|---|---|
| | Form of p55 | Serum Titer [GMT/(SE)] | |
| Group | DNA Antigen | 4wp1 | 2wp2 |
| 1 | adsorbed on PLG/CTAB (burst free) particles | 25 (52) | 23,900 (3326) |
| 2 | adsorbed on PLG/CTAB particles | 13 (6) | 11,800 (3242) |
| 3 | adsorbed on PLG/CTAB particles (non-freeze dried) | 8 (3) | 8,877 (1964) |
| 4 | adsorbed on MF59/DOTAP 40 emulsion (1 µg) | 5 (8) | 5,141 (2950) |
| 5 | adsorbed on MF59/DOTAP 40 emulsion (10 µg) | 135 (74) | 38,100 (6150) |
| 6 | adsorbed on MF59/DOTAP 80 emulsion (1 µg) | 22 (33) | 8,901 (4067) |
| 7 | adsorbed on MF59/DOTAP 80 emulsion (10 µg) | 147 (70) | 75,900 (6992) |
| 8 | free (1 µg) | 4 (1) | 7 (18) |
| 9 | free (10 µg) | 49 (64) | 1,995 (2052) |
| 10 | adsorbed on MF59 emulsion (10 µg) | 13 (11) | 6,690 (2592) |

Example 24

Microparticle Induction of Immune Response in Guinea Pigs

PLG/CTAB microparticles with adsorbed gp120 DNA were formed as described above in the previous examples. Other samples are as shown below in Table 20, and included the microparticles with and without aluminium phosphate, controls of free soluble gp120, with and without aluminium phosphate, and MF59 protein, encoded by gp120 DNA. IM immunization of guinea pigs and antibody induction (collection and analysis of serum) were performed as described in the previous examples. The results are shown in Table 21 below.

TABLE 21

| Formulation | GMT | SE |
|---|---|---|
| PLG/CTAB gp120 adsorbed (25 µg) | 1435 | 383 |
| PLG/CTAB gp120 adsorbed (25 µg) + Alum. phosphate | 3624 | 454 |
| soluble gp120 DNA (25 µg) + Alum phosphate | 119 | 606 |
| soluble gp120 DNA (25 µg) alone | 101 | 55 |
| MF59 protein (50 µg) | 3468 | 911 |

Example 25

Intranasal (IN) Immunization with p55 DNA Adsorbed Microparticles

PLG/CTAB microparticles with adsorbed p55 DNA, and PLG/DDA microparticles with adsorbed p55 DNA, were formed as described above in the previous examples. IN immunization of mice with 25 or 100 µg, antibody induction (collection and analysis of serum), and CTL induction were performed as described in the previous examples, at two and four weeks post $1^{st}$ immunization (2wp1, 4wp1), two and four weeks post $2^{nd}$ immunization (2wp2, 4wp2), and two and four weeks post $3^{rd}$ immunization (2wp3, 4wp3). Controls included immunization with soluble p55 DNA alone or with 10 µg cholera toxin. The results for antibody induction are shown in Table 22, and the results for lysis by CTL (at 4 weeks post $4^{th}$ immunization) are shown in Table 23 below.

TABLE 22

| Formulation | 2wp1 | 4wp2 | 2wp2 | 4wp2 | 2wp3 | 4wp3 |
|---|---|---|---|---|---|---|
| PLG/CTAB with p55 DNA adsorbed (25 µg) | 189 | 529 | 1412 | 882 | 908 | 742 |
| PLG/CTAB with p55 DNA adsorbed (100 µg) | 128 | 383 | 3462 | 2887 | 289000 | 134000 |
| PLG/DDA with p55 DNA adsorbed (25 µg) | 247 | 482 | 1223 | 338 | 940 | 545 |
| PLG/DDA with p55 DNA adsorbed (100 µg) | 143 | 1351 | 2538 | 1341 | 357000 | 161000 |
| soluble p55 DNA (100 µg) + cholera toxin (10 µg) | 195 | 270 | 2298 | 617 | 1549 | 862 |
| soluble p55 DNA (100 µg) alone | 362 | 260 | 618 | 190 | 285 | 263 |

TABLE 23

PERCENT SPECIFIC LYSIS OF TARGETS

| Group | Formulation | Dose of p55 DNA | Target Ratio | SvB pGAG[a] | SvB P7g+[b] |
|---|---|---|---|---|---|
| 1 | PLG/CTAB with adsorbed p55 DNA | 100 µg | 60 | −1 | 82 |
| | | | 15 | −1 | 53 |
| | | | 4 | 12 | 25 |
| 2 | PLG/DDA with adsorbed p55 DNA | 100 µg | 60 | 10 | 47 |
| | | | 15 | 3 | 26 |
| | | | 4 | 2 | 8 |
| 3 | p55 DNA plus cholera toxin (10 µg) | 100 µg | 60 | 9 | 64 |
| | | | 15 | 2 | 22 |
| | | | 4 | 0 | 7 |
| 4 | p55 DNA alone | 100 µg | 60 | 4 | 6 |
| | | | 15 | 2 | 3 |
| | | | 4 | 1 | 1 |

[a]SvB cell line pulsed with irrelevant peptide
[b]SvB cell line pulsed with p7g peptide

Example 26

Preparation of Adjuvant Compositions

MTP-PE was provided by CIBA-GEIGY (Basel, Switzerland). Squalene and TWEEN® 80 were obtained from Sigma Chemical Co. (St. Louis, Mo.). CFA and IFA were obtained from Gibco (Grand Island, N.Y.). Aluminum hydroxide (Rehsorptar) was obtained from Reheis Chemical Co. (Berkeley Heights N.J.).

Preparation of oil droplet emulsions was made by a number of methods. In the first method, a mixture consisting of 4% squalene, 0.008% TWEEN® 80, 250 µg/ml MTP-PE and antigen in phosphate buffered saline (PBS) was passed through a 23 gauge needle 6 times. This emulsion consisted of oil droplet sizes in the range of 10 microns and is termed MTP-PE-LO. The second method comprises passing the above-described mixture through a Kirkland emulsifier five times. This emulsion consists of oil droplets primarily of 1-2 microns and is termed MTP-PE-LO-KE. The Kirkland emulsifier (Kirkland Products, Walnut Creek, Calif.) is a small-scale version of the commercial knife-edged homogenizer (e.g., Gaulin Model 30CD and Rainnie Minilab Type 8.30H) generating about 1000 psi in the working chamber. In the third method, mixtures containing 0.3-18% squalene and 0.2-1.0 mg/ml MTP-PE with or without TWEEN®80 were passed through the Microfluidizer (Model No. 110Y Microfluidics, Newton, Mass.) at 5,000-30,000 psi. Typically, 50 ml of emulsion was mixed for 5 minutes or 100 ml for 10 minutes in the microfluidizer. The resulting emulsions consisted of oil droplets of 100-750 nm depending on squalene, MTP-PE, and detergent concentration and microfluidizer operating pressure and temperature. This compositions is termed MTP-PE-LO-MF.

Example 27

Preparation of Microparticles Using CTAB

Blank microparticles were produced using CTAB as follows. Solutions used:
(1) 4% RG 504 PLG (Boehringer Ingelheim) in dimethyl chloride.
(2) 0.5% CTAB (Sigma Chemical Co., St. Louis, Mo.) in water.

In particular, the microparticles were made by combining 12.5 ml of polymer solution with 1.25 ml of distilled water and homogenizing for 3 minutes using an Omni benchtop homogenizer with a 10 mm probe at 10K rpm to form a w/o emulsion. The w/o emulsion was added to 50 ml of the 0.5% CTAB solution and homogenized for 3 minutes to form a w/o/w emulsion. The w/o/w emulsion was left stirring overnight for solvent evaporation, forming microparticles. The formed microparticles were then filtered through a 38μ mesh, washed with water by centrifugation 4 times, and lyophilized. The microparticles were then sized in a Malvern Master sizer for future use.

Example 28

Effect of MPL and CpG Oligonucleotides on Immune Response Phenotype

Groups of 10 mice were immunized as follows: Group 1) MF59 with recombinant HIV p55 gag protein in the presence and absence of CpG oligonucleotides; Group 2) MF59 incorporating monophosphoryl lipid A (MPL) with HIV p55 gag protein; Group 3) SDS/PLG microparticles with HIV p55 gag protein adsorbed to the surface in the presence and absence of CpG oligonucleotides; Group 4) SDS/PLG p55 adsorbed microparticles with MPLs; Group 5) recombinant protein with MPL; and Group 6) recombinant protein alone. The MF59 dose was 25 μl per animal, HIV p55 protein was 25 μg per animal, CpG oligonucleotide was 50 μg per animal, and MPL was given at 10 μg per animal. The microparticles were given at a dose containing 25 μg of protein.

MPL was obtained from Ribi Immunochem Res. Inc. (Hamilton, Mont.). MPL/MF59 was prepared by dissolving MPL in $CHCl_3$, transferring the solution into Squalene/Span85 and formulating the standard MF59 emulsion with Tween80/$H_2O$.

Recombinant yeast p55 gag protein was produced by standard fermentation techniques well known to those skilled in the art in which yeast are disrupted by dynomill. The p55 protein was extracted from pelleted material obtained from the cell lysate in urea/NaCl buffer. The urea soluble protein was purified to >90% homogeneity by anion-exchange chromatography in the presence of 6M urea.

Figure 2:
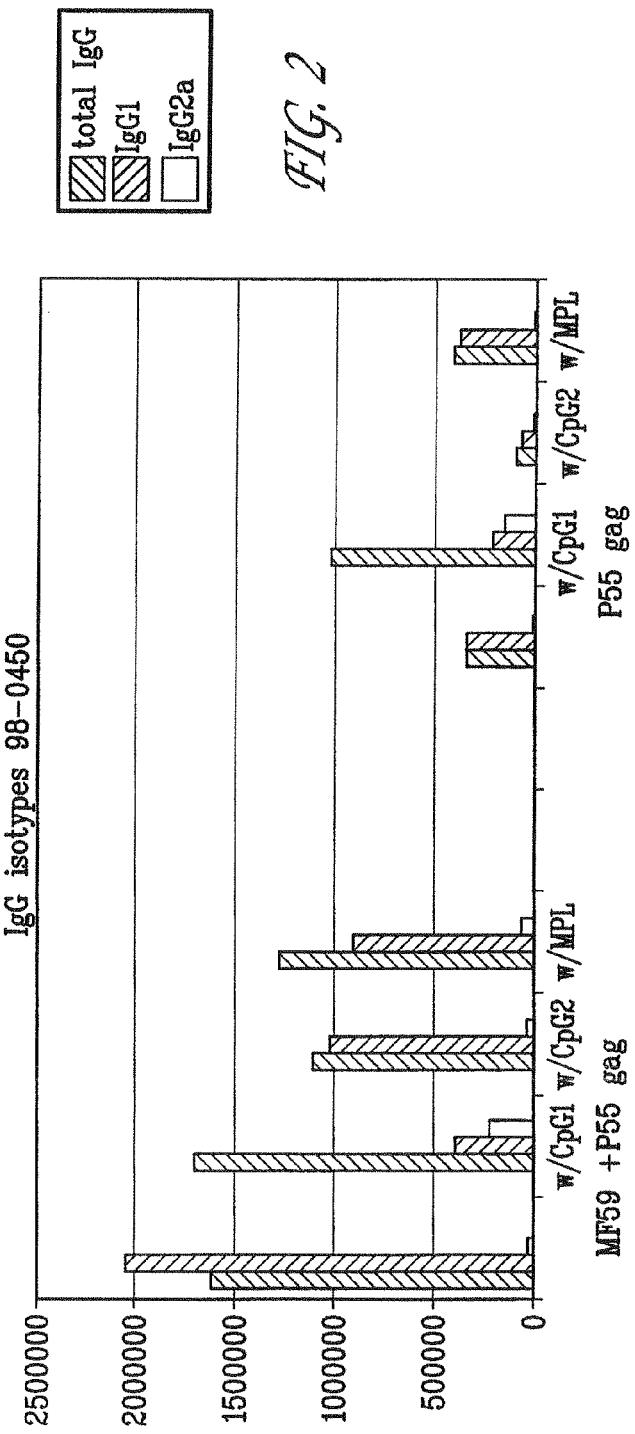
FIG. 2 is a bar graph showing typical results of immunoglobulin isotypes generated by preferred immunogenic compositions comprising MF59 adjuvant according to the invention.

Mice received three intramuscular injections at weekly intervals, and serum samples were collected two weeks post third injection and assayed for total IgG (G+M+A), IgG1 and IgG2a using a chemiluminescent ELISA assay based upon CA Aequorn (Sealite Inc., Norcross, Ga.). Results from a typical assay are shown in FIGS. 1 and 2. In the case of the adsorbed microparticles, animals receiving the CpG oligonucleotides showed an IgG2a response 19-fold higher than that of the adsorbed particles alone, 7-fold higher response than adsorbed particles with MPLs, and 17-fold higher response than protein alone. In the case of the protein with MF59, animals receiving the CpG oligonucleotides showed an IgG2a response 7-fold higher than that induced in the absence of the CpG oligonucleotides, 2.6-fold higher than the combination of MF59 and MPLs, 15-fold higher than protein with MPLs, and 23-fold higher than protein alone. The results indicate that CpG oligonucleotides in combination with either MF59 or PLG microparticles stimulate a Th1 lymphocyte response which is significantly greater than the response induced by MPLs with either MF59 or PLG microparticles.

Oligonucleotides were prepared by Oligos Etc., Inc. (Wilsonville, Oreg.). CpG1 comprises SEQ ID NO:28. CpG2 comprises the non-CpG sequence tccaggacttctctcaggtt (SEQ ID NO:29).

Example 29

IM Immunization of p55 gag Protein and Various Adjuvants

Groups of 9 mice were immunized intramuscularly, except where noted, as follows: Group 1) MF59 with recombinant HIV p55 gag protein, and DOTAP 80 in the presence of CpG1 oligonucleotide; Group 2) MF59 with recombinant HIV p55 gag protein, and DOTAP 160 in the presence of CpG1 oligonucleotide; Group 3) MF59 with recombinant HIV p55 gag protein and DOTAP; Group 4) MF59 with recombinant HIV p55 gag protein; Group 5) MF59 with recombinant HIV p55 gag protein in the presence of CpG1 oligonucleotide; Group 6) recombinant HIV p55 gag protein and DOTAP 160; Group 7) recombinant HIV p55 gag protein and CpG1 oligonucleotide; Group 8) recombinant HIV p55 gag protein, and DOTAP 160 in the presence of CpG1 oligonucleotide; and Group 9) vv-gag-pol ($2 \times 10^7$ pfu) IP. The MF59 dose was 25 μl per animal, HIV p55 protein was 25 μg per animal, and CpG oligonucleotide was 50 μg per animal. Following immunization, serum anti-p55 IgG titer was measured, the results of which appear in FIG. 3. As can be seen, antibody titer in the presence of a positively charged emulsion (with DOTAP) is twice as high as in the absence of a positively charged emulsion (without DOTAP). Lysis of targets (SvB cell line) by CTL was also measured with each group, the results of which appear in FIG. 4. As can be seen, addition of DOTAP to result in a positively charged emulsion increases the CTL response.

Example 30

Ionic Emulsion Adjuvants

Submicron emulsions containing ionic surfactants were formulated using a nonionically-stabilized MF59 formulation. Several ionic surfactants were tested for solubility in squalene. Three ionic detergents Dioleoyl-3-Trimethylammonium-Propane (DOTAP), Dioleoyl-sn-Glycero-3-Ethylphosphocholine (DEPC) and dioleoyl-phosphatidic acid (DPA) were found to be soluble in squalene. Prototypic ionic emulsions were formulated by dissolving each of the detergents in squalene/10% Span 85 at concentrations ranging from 4-52 mg/ml squalene. The squalene/surfactant mixtures were emulsified with 0.5% Tween 80/$H_2O$ at 5 ml squalene/100 ml $H_2O$. A pre-emulsion was formed by homogenization with a Silverson homogenizer (5 minutes, 5000 RPM) and the final emulsions were made by microfluidization (~10,000 psi, 5 passes, Microfluidizer 110S). Emulsions of each type were tested for droplet size and Zeta-potential. The results are shown in Table 24 below.

TABLE 24

| Emulsion | Mean droplet size (nm) | Zeta potential (mv) |
|---|---|---|
| MF/DOTAP/160 | 210 | +51 |
| MF/DOTAP/160/CpG | 171 | −2 |
| MF/DOTAP/80 | 145 | +42 |
| MF/DEPC/160 | 168 | +26.5 |
| MF/DPA/160 | 162 | −35.7 |
| MF59 | ~150 | −20 |

MF59/DOTAP/160 and MF59/DOTAP/80 were tested for binding of both DNA and CpG ODN. Two MF59/DOTAP formulations, 160 mg/100 ml DOTAP and 80 mg/100 ml DOTAP, were used to adsorb p55 DNA. The emulsions were each incubated with DNA at 50 ug/ml, 100 ug/ml and 200 ug/ml overnight at 4 C. A control of MF59/water with no DOTAP was also incubated with 50, 100 and 200 ug DNA. The emulsions were centrifuged using the air fuge, and the subnatant for each sample was acid hydrolyzed and run on the DNA assay. (Since there was enough turbidity to interfere in A260 measurements). The MF59 without DOTAP control samples were used to establish a standard curve from which the amount of DNA left in the subnatant of the MF59/DOTAP samples was calculated, the results of which are shown in Table 25 below.

TABLE 25

| Formulation | μg DNA input | actual μg adsorbed | % efficiency |
|---|---|---|---|
| 59/160 | 50 | 49.7 | 99.56 |
| 59/160 | 100 | 99.6 | 99.6 |
| 59/160 | 200 | 132 | 66 |
| 59/80 | 50 | 48.5 | 97 |
| 59/80 | 100 | 67.6 | 67.6 |
| 59/80 | 200 | 73 | 36 |

MF59 was made with DOTAP in the squalene. This was incubated with 0.5 mg/ml CpG overnight, the next day the emulsion was centrifuged in an eppindorf centrifuge for 50 min., and the subnatant was run on a GPC column. 0.5/ml CpG was added to regular MF59 and spun down then analyzed on the column. The amount of CpG in the MF59/Dotap subnatant was 50% of that in the MF59 spiked with CpG, indicating that nearly 50% of the CpG input is actually in the oil phase.

An adsorption isotherm was done next, where CpG was added to MF59/Dotap at 100 ug/ml, 500 ug/ml, 1 mg/ml and 2 mg/ml. This was left at 4 C for about 4 days, then samples were centrifuged in an air-fuge, along with MF59 spiked with 0.5 mg/ml CpG.

The subnatant (which was very clear), was run on a GPC column along with a standard curve made with the spiked MF59 at 0.5 ug, 10 ug, 5 ug, 10 ug and 20 ug. Percentage adsorption was measured and the results are shown in Table 26 below.

TABLE 26

| μg/ml CpG input | % adsorbed |
|---|---|
| 100 | 100 |
| 500 | 97 |
| 1000 | 65 |
| 2000 | 42 |

We claim:

1. A method of inducing an immune response in a host animal comprising administering to said animal a microemulsion having an adsorbent surface, said microemulsion comprising a microdroplet emulsion comprising:

(a) a metabolizable oil; and
(b) an emulsifying agent;
wherein, said emulsifying agent comprises a detergent.

2. The method of claim 1, wherein said oil and said emulsifying agent are present in the form of an oil-in-water emulsion having oil droplets, wherein substantially all of the oil droplets are less than 1 micron in diameter, and wherein said microemulsion exists in the absence of a polyoxypropylene-polyoxyethylene block copolymer.

3. The method of claim 2, wherein said oil is a member of the group consisting of an animal oil, an unsaturated hydrocarbon, a terpenoid, and a vegetable oil.

4. The method of claim 3, wherein said oil is a terpenoid which is squalene.

5. The method of claim 2, wherein said microemulsion comprises 0.5 to 20% by volume of said oil in an aqueous medium.

6. The method of claim 1, wherein said microemulsion comprises 0.01 to 0.5% by weight of said emulsifying agent.

7. The method of claim 1, wherein said emulsifying agent comprises a non-ionic detergent.

8. The method of claim 7, wherein said emulsifying agent comprises a polyoxyethylene sorbitan mono-, di-, or triester or a sorbitan mono-, di-, or triether.

9. The method of claim 1, wherein said emulsifying agent comprises a cationic detergent.

10. The method of claim 9, wherein said cationic detergent is selected from the group consisting of hexadecyltrimethylammonium bromide, benzalkonium chloride, dimethyl dioctodecyl ammonium bromide, DOTAP, dodecyltrimethylammonium bromide, benzyldimethylhexadecyl ammonium chloride, cetylpyridinium chloride, methylbenzethonium chloride, and 4-picoline dodecyl sulfate.

11. The method of claim 9, wherein said microemulsion comprises 0.01 to 0.5% by weight of said emulsifying agent.

12. The method of claim 1, wherein said emulsifying agent comprises an anionic detergent.

13. The method of claim 1, wherein said microemulsion further comprises a biologically active macromolecule adsorbed on the surface thereof, wherein the biologically active macromolecule is at least one member selected from the group consisting of a polypeptide, a polynucleotide, a polynucleoside, an antigen, an immunomodulator, and an adjuvant.

14. The method of claim 13, wherein said macromolecule is an adjuvant selected from the group consisting of a CpG oligonucleotide, alum, a bacterial cell wall component, and muramyl peptide.

15. The method of claim 1, wherein said host animal is a mammal

16. The method of claim 15, wherein said mammal is a human.

* * * * *

UNITED STATES PATENT AND TRADEMARK OFFICE
CERTIFICATE OF CORRECTION

PATENT NO.         : 8,734,832 B2
APPLICATION NO.    : 13/621174
DATED              : May 27, 2014
INVENTOR(S)        : Derek O'Hagan et al.

It is certified that error appears in the above-identified patent and that said Letters Patent is hereby corrected as shown below:

Title Page

Item (73): Assignee
Please change: "Novartis AG, Basel (CH)" to --Novartis Vaccines and Diagnostics, Inc., Emeryville, CA--

Signed and Sealed this
Tenth Day of May, 2016

Michelle K. Lee
*Director of the United States Patent and Trademark Office*